US010748663B2

(12) United States Patent
Kalafatis

(10) Patent No.: US 10,748,663 B2
(45) Date of Patent: Aug. 18, 2020

(54) MACHINE LEARNING, NATURAL LANGUAGE PROCESSING AND NETWORK ANALYSIS-GUIDED DISCOVERY RELATED TO MEDICAL RESEARCH

(71) Applicant: Efthymios Kalafatis, Piraeus (GR)

(72) Inventor: Efthymios Kalafatis, Piraeus (GR)

(*) Notice: Subject to any disclaimer, the term of this patent is extended or adjusted under 35 U.S.C. 154(b) by 304 days.

(21) Appl. No.: 15/966,454

(22) Filed: Apr. 30, 2018

(65) Prior Publication Data

US 2018/0322958 A1 Nov. 8, 2018

Related U.S. Application Data

(60) Provisional application No. 62/501,129, filed on May 4, 2017.

(51) Int. Cl.
*G06F 16/00* (2019.01)
*G16H 50/70* (2018.01)
(Continued)

(52) U.S. Cl.
CPC .............. *G16H 50/70* (2018.01); *G06F 7/08* (2013.01); *G06F 16/2465* (2019.01);
(Continued)

(58) Field of Classification Search
CPC .......... G06N 5/003; G06N 20/00; G06N 3/08; G06F 16/2465; G06F 16/34; G06F 16/36;
(Continued)

(56) References Cited

U.S. PATENT DOCUMENTS 6,728,642 B2 * 4/2004 Bloch ................... G16B 40/00
702/20
7,991,733 B2 * 8/2011 Mons ...................... G06F 16/36
707/603
(Continued)

FOREIGN PATENT DOCUMENTS

WO WO-2015/021404 A2 2/2015

OTHER PUBLICATIONS

Ching-Wu Cheng, Hong-Qing Yao and Tsung-Chih Wu, "Applying data mining techniques to analyze the causes of major occupational accidents in the petrochemical industry", pp. 1269-1278 (Year: 2013).*

*Primary Examiner* — Merilyn P Nguyen
(74) *Attorney, Agent, or Firm* — Franco De Liguori; DP IP Group

(57) ABSTRACT

Techniques are disclosed for discovering, biological elements, functions and pathways, and environmental and nutritional factors related to diseases and medical syndromes. The techniques preprocess database query results and harmonize data using natural language processing before transforming them into the frequency space. The transformed results are analyzed with various categories of machine learning algorithms whose results are normalized, ranked and selectively combined, weighted or un-weighted, to produce a single result ranking the most important elements affecting a target disease or medical syndrome. The invention also uses alternative algorithms producing hypotheses on associations between medical topics, which are used as suggestions for exploratory medical research.

20 Claims, 8 Drawing Sheets

(51) Int. Cl.
*G06N 5/04* (2006.01)
*G06F 7/08* (2006.01)
*G06N 20/00* (2019.01)
*G06F 16/2458* (2019.01)
*G06F 16/2457* (2019.01)
*G06N 20/10* (2019.01)
*G06N 3/08* (2006.01)
*G06N 5/00* (2006.01)
*G06N 3/00* (2006.01)
*G06N 20/20* (2019.01)

(52) U.S. Cl.
CPC ....... *G06F 16/24578* (2019.01); *G06N 5/041* (2013.01); *G06N 20/00* (2019.01); *G06F 2207/4824* (2013.01); *G06N 3/006* (2013.01); *G06N 3/08* (2013.01); *G06N 5/003* (2013.01); *G06N 20/10* (2019.01); *G06N 20/20* (2019.01)

(58) Field of Classification Search
CPC .... G06F 16/367; G06F 16/954; G06F 16/958; G06F 7/08
See application file for complete search history.

(56) References Cited

U.S. PATENT DOCUMENTS

| | | | |
|---|---|---|---|
| 8,145,582 B2* | 3/2012 | Angell | G16H 50/70 706/45 |
| 8,280,640 B2* | 10/2012 | Levin | G06F 7/02 702/19 |
| 2005/0060305 A1* | 3/2005 | Hopkins | G06Q 50/22 |
| 2008/0306918 A1* | 12/2008 | Mons | G06F 16/36 |
| 2008/0306926 A1* | 12/2008 | Friedlander | G06Q 50/24 |
| 2010/0004874 A1 | 1/2010 | Rzhetsky et al. | |
| 2010/0049095 A1* | 2/2010 | Bunn | A61B 5/1117 600/595 |
| 2010/0070448 A1* | 3/2010 | Omoigui | H01L 27/14647 706/47 |
| 2013/0132309 A1 | 5/2013 | Kvernvik et al. | |
| 2013/0241719 A1* | 9/2013 | Biswas | G06F 19/3418 340/407.1 |
| 2015/0149461 A1 | 5/2015 | Aguilar Lemarroy et al. | |
| 2016/0094422 A1 | 3/2016 | Poola et al. | |
| 2016/0378945 A1* | 12/2016 | Mian | G16H 10/60 705/3 |

\* cited by examiner

MACHINE LEARNING, NATURAL LANGUAGE PROCESSING AND NETWORK ANALYSIS-GUIDED DISCOVERY RELATED TO MEDICAL RESEARCH

CROSS-REFERENCE TO RELATED APPLICATIONS

This application claims the benefit of U.S. Provisional Application No. 62/501,129, filed on May 4, 2017, which is incorporated herein by reference in its entirety.

BACKGROUND

Field of the Disclosure

The present invention relates to a computer-implemented method, a computer, and a non-transitory computer medium using data preprocessing and a combination of data mining techniques for discovering biological elements, functions and pathways, and environmental and nutritional factors related to diseases, and medical syndromes.

Background of the Disclosure

During the last two decades biomedical research has significantly advanced and many discoveries have been achieved with the help of emerging technologies. Digital 3D imaging techniques have been used to collect anatomical and functional data while genetics and gene analysis with the use of biomarkers and other techniques have been employed in the understanding of genetic mechanisms and mapping of the genetic profile of individuals.

Recent developments have boosted research in identifying genes related to diseases and medical syndromes (i.e. a set of medical signs and symptoms that are correlated with each other and may occur in more than one disease). At the same time, serious effort is put into linking the genetic profile of individuals and their diseases and/or syndromes and proposing a personalized treatment that is expected to bring superior results than traditional treatments.

The use of mathematical and statistical methods together with computing has boosted the analysis of huge data sets from medical databases and other sources and has facilitated the extraction of new knowledge (e.g. gene association to diseases and syndromes) which is then tested and experimentally validated.

Among the most popular techniques in this field is Data Mining (DM) which is used to discover patterns in large data sets. DM uses techniques of Artificial Intelligence (AI), Machine Learning (ML), statistics, and database systems. DM typically involves identifying unusual data records (i.e. outliers and deviations) in the data sets and relationships between variables (i.e. association rule learning), discovering similar groups and structures in the data (i.e. clustering), generalizing known structures to apply to new data (i.e. classification), finding a function that models the data with the minimum error (i.e. regression), and data visualization and reporting in a compact way that is easier to grasp (i.e. summarization).

As a general rule data processing includes the steps of:
  preprocessing (to filter out outliers and other data of no real value)
  transformation (to transform the preprocessed data into a different feature space and/or dimension that is easier to further process and extract knowledge out of it)
  DM (to identify patterns in the transformed data)
  interpretation (to extract knowledge out of the identified patterns)
  evaluation (to assess the importance or value of the interpretation results, especially in the case where multiple DM/ML techniques have been used, each producing partial results or an interpretation of the same results from a different viewpoint) and
  creation of knowledge (by selecting and combining the most appropriate results of the evaluation step).

Various algorithms have been proposed for the previous ML steps. Among the most widely used are Decision Trees (DT), Rule Learning, and Instance Based Learning (IBL), such as k-Nearest Neighbors (k-NN), Genetic Algorithms (GA), Artificial Neural Networks (ANN), Random Forests (RF), and Support Vector Machines (SVM), which fall into the category of Supervised ML where the system must learn a target function, that is a function describing the data.

Mixture models, ANN, Hebbian Learning, Expectation-Maximization algorithm (EM), and Singular Value Decomposition (SVD) are commonly used for Unsupervised ML where the system tries to describe the hidden function in unlabeled, i.e. unclassified and uncategorized data.

Brute force, Value function approaches, Monte Carlo methods, Temporal Difference methods, and Direct Policy Search are used in Reinforcement Learning, where the system attempts to learn through direct interaction with its unknown environment so as to maximize some notion of cumulative reward.

Various other methods instead of ML have been tested like Feature Selection which selects a subset of features from the feature space, which is more relevant and informative for the construction of a model. Another alternative method gaining popularity in medical knowledge discovery is the Network Analysis (NA) where networked structures are characterized in terms of nodes, edges and links. It started from the development of social networks but has found applications in biomedical data and many other areas. It uses network and graph theories.

Other approaches concentrate on preprocessing database entries and applying normalization to condition the data prior to using any of the above methods so as to increase their performance.

SUMMARY

The present disclosure describes techniques for discovering biological elements, functions and pathways, and environmental and nutritional factors related to diseases, and medical syndromes, as well as, supporting exploratory Biomedical Research.

In one embodiment, the invention describes a technique which applies preprocessing to the results obtained from querying medical databases for medical topics like genes, biological pathways, conditions, and environmental and nutritional factors, etc. These results are homogenized using Information Extraction, natural language processing and understanding techniques to allow for different forms of the same medical etc. term to be converted into a standard form across all occurrences. In cases where research involves a specific syndrome or disease, the technique further converts the homogenized results into the frequency space by calculating the frequency of occurrence of each term across all returned records, i.e. scientific abstracts from the database query, which results are then normalized, ranked and selectively combined to produce a single result ranking the most important elements affecting a target disease or medical syndrome. Individual results are also produced, which take the form of hypothetical associations between medical topics, and which individual results are used as suggestions for exploratory medical research.

In another embodiment, the invention provides a methodology which substitutes natural language processing with other lexical and grammatical processing.

In yet another exemplary embodiment, multiple data mining algorithms of the same category are used and normalization is performed to make results with limited confidence data or limited confidence spacing between topics suitable for combination into the single final result.

In a variation of these exemplary embodiments, the partial results obtained from each data mining algorithm is weighted according to one or more characteristics of the results so as to take into account the importance and confidence of the individual results in calculating the combined end result.

BRIEF DESCRIPTION OF THE TABLES

Figure 1:
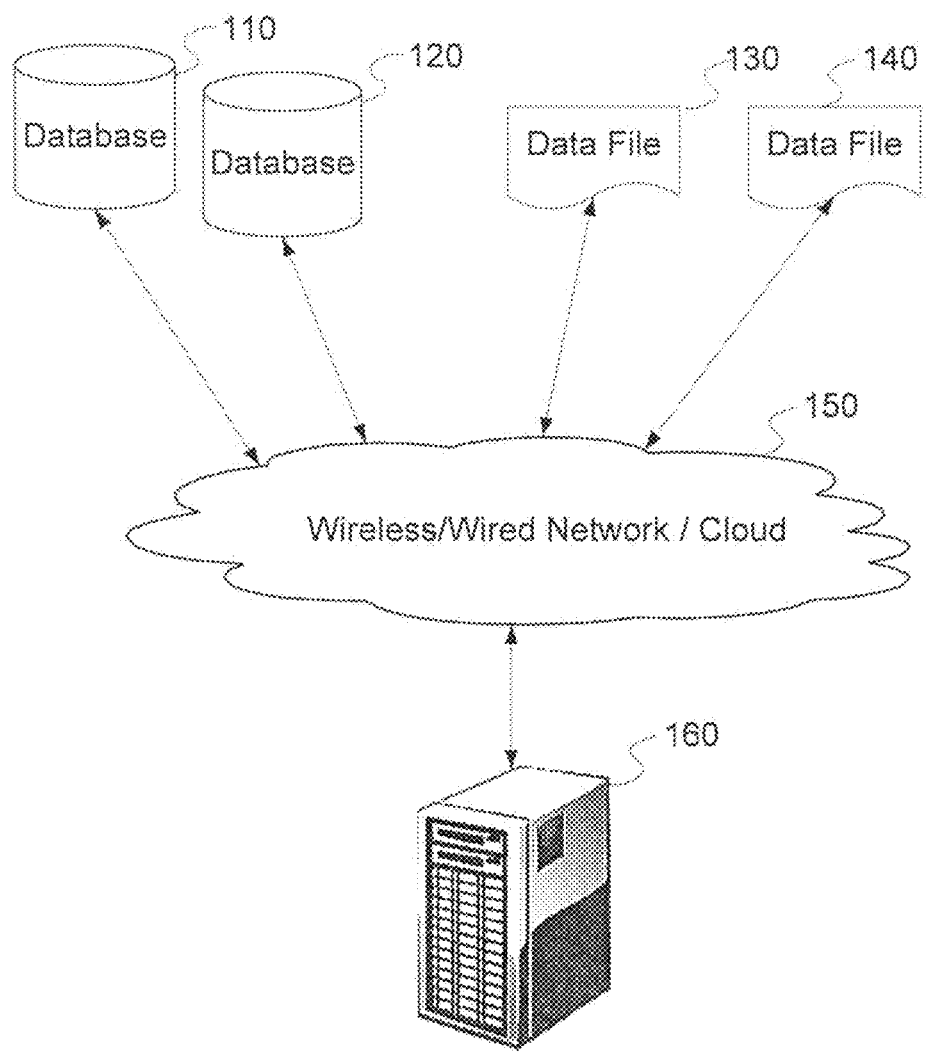
FIG. 1 shows an exemplary computing system implementing the present invention.

Table 1: Frequency of Occurrence of Medical Term "histidine" in .CSV files
Table 2: Pearson's Product Moment Correlation Matrix
Table 3: Correlation Pairs having Pearson correlation >T2
Table 4: Weighted Degree measure for the graph of FIG. 7
Table 5: Example T/F table
Table 6: Example T/F Pearson's Product Moment Correlation Matrix
Table 7: Example partial results 672, 674, 676, 678 outputted from various algorithms.

DETAILED DESCRIPTION

The word "exemplary" is used herein to mean "serving as an example, instance, or illustration". Any embodiment described herein as "exemplary" is not necessarily to be construed as preferred or advantageous over other embodiments.

The terms "network", "computer network", "wireless network", "wired network", "Internet", "Intranet", and "Cloud" are used interchangeably and have the same meaning (that of a means for connecting two computers or other computer-related entities together for the exchange of data, commands and other control information, unless explicitly) otherwise mentioned.

The terms "medical", "biological", and "biomedical" are used interchangeably and have the same meaning in the realm of the present discussion and claims, unless explicitly mentioned otherwise.

The acronym "DM" is intended to mean "Data Mining".
The acronym "AI" is intended to mean "Artificial Intelligence".
The acronym "ML" is intended to mean "Machine Learning".
The acronym "DT" is intended to mean "Decision Trees".
The acronym "IBL" is intended to mean "Instance Based Learning".
The acronym "k-NN" is intended to mean "k-Nearest Neighbors".
The acronym "IF" is intended to mean "Information Extraction".
The acronym "GA" is intended to mean "Genetic Algorithms".
The acronym "ANN" is intended to mean "Artificial Neural Networks".
The acronym "RF" is intended to mean "Random Forests".
The acronym "SVM" is intended to mean "Support Vector Machines".
The acronym "EM" is intended to mean "Expectation-Maximization".
The acronym "SVD" is intended to mean "Singular Value Decomposition".
The acronym "NA" is intended to mean "Network Analysis".
The acronym "OS" is intended to mean "Operating System".
The acronym "NLP" is intended to mean "Natural Language Processing".
The acronym "NLU" is intended to mean "Natural Language Understanding".
The acronym "mRMR" is intended to mean "Minimum-Redundancy-Maximum-Relevance".
The acronym "CSV" is intended to mean "Comma-Separated Values".
The acronym "P450scc" is intended to mean "Cholesterol Side-Chain Cleavage Enzyme".
The acronym "AdaBoost" is intended to mean "Adaptive Boosting".
The acronym "RCA" is intended to mean "Root Cause Analysis".
The acronym "JNK" is intended to mean "Jun amino-terminal Kinases".
The acronym "atf6" is intended to mean "activating transcription factor 6".
The acronym "ER" is intended to mean "Endoplasmic Reticulum".
The acronym "UPR" is intended to mean "Unfolded Protein Response".
The acronym "CHOP" is intended to mean "C/EBP homologous protein".
The acronym "C/EBP" is intended to mean "CCAAT-enhancer-binding protein".
The acronym "DNA" is intended to mean "Deoxyribonucleic acid".
The acronym "SMOTE" is intended to mean "Synthetic Minority Oversampling Technique".
The acronym "ADASYN" is intended to mean "ADAptive SYNthetic".
The acronym "PRIM" is intended to mean "Patient Rule Induction Method".

The acronym "NRF1" is intended to mean "Nominal Response Feature 1 (T/F values)" and represents any Medical Topic such as disease, individual Symptom (not grouped Symptoms!), Gene, Pathway etc.

The acronym "NRF2" is intended to mean "Nominal Response Feature 2 (T/F values)" and represents a group of Symptoms that are usually present to a Syndrome or Disease.

The acronym "ASSOC" is intended to mean "Associations Rule Algorithm".

The acronym "CLUS" is intended to mean "Cluster Analysis algorithm".

The acronym "CL1" is intended to mean "Classification Analysis Algorithm 1".

The acronym "CL2" is intended to mean "Classification Analysis Algorithm 2".

The acronym "CD" is intended to mean "Community Detection Algorithm".

The acronym "HS1" is intended to mean "HOTSPOT Algorithm 1".

The acronym "HS2" is intended to mean "HOTSPOT Algorithm 2".

The acronym "FS1" is intended to mean "Feature Selection Algorithm 1".

The acronym "FS2" is intended to mean "Feature Selection Algorithm 2".

The acronym "FS3" is intended to mean "Feature Selection Algorithm 3".

The term "computing device" may be used interchangeably with "client device", "mobile device", "computing system", "computer system", "server", "networked device", "networked computing device", "networked computer system", and "networked computing system", unless otherwise stated or implied by the particular context it occurs or refers to.

A "disease" is a particular abnormal condition, a disorder of a structure or function that affects part or all of an organism.

A "syndrome" is a set of medical signs and symptoms that are correlated with each other.

A "gene" is a locus (or region) of DNA which is made up of nucleotides and is the molecular unit of heredity.

A "DNA" or "deoxyribonucleic acid" is a long molecule that contains our unique genetic code. Like a recipe book it holds the instructions for making all the proteins in living organisms.

A "biological pathway is a series of actions among molecules in a cell that leads to a certain product or a change in a cell. Such a pathway can trigger the assembly of new molecules, such as a fat or protein. Pathways can also turn genes on and off, or spur a cell to move. Some of the most common biological pathways are involved in metabolism, the regulation of gene expression and the transmission of signals. Pathways play key role in advanced studies of genomics.

As used herein and in the appended claims, the singular forms "a", "and", and "the" include plural referents unless the context clearly dictates otherwise. Thus, for example, reference to "a protein" includes a plurality of proteins and reference to "protein-protein interactions" generally includes reference to one or more interactions and equivalents thereof known to those skilled in bioinformatics and/or molecular biology.

Unless defined otherwise, all technical and scientific terms used herein have the same meaning as commonly understood to one of ordinary skill in the art to which this invention belongs (systems biology, bioinformatics).

Although any methods similar or equivalent to those described herein can be used in the practice or testing of the invention, the preferred methods are described.

All publications mentioned herein are incorporated by reference in full for the purpose of describing and disclosing the databases and methodologies, which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The present invention treats the problem of discovering biological elements (e.g. genes, proteins, biomarkers, biomolecules, biological pathways, biological functions, environmental factors, nutritional factors, etc.) that are associated with diseases and medical syndromes. It analyzes scientific publications and data stored in medical databases to extract information and uses one or more algorithms (like natural language processing, data mining, machine learning, network analysis, root cause analysis, statistical processing, etc.) to extract knowledge and improve on the accuracy of single-method approaches.

The novelty of the present invention lies on the combination of a variety of techniques aiming at analyzing various aspects of medical data for extracting knowledge needed to associate diseases and medical syndromes with particular biological elements and environmental and nutritional factors. In addition, it also identifies direct and indirect associations between medical topics and also identifies several associated Topics using Clustering Algorithms.

In particular, the present invention employs preprocessing and frequency analysis on raw medical data to transform them into a format suitable for use by one or more data mining algorithms used to extract knowledge. The partial results from each data mining algorithm provide different insights and knowledge aspects of the transformed data and are then combined into a final result using a variety of normalization and scoring techniques.

The invention provides a novel framework for identifying, normalizing, and extracting data from scientific publications, analyzing them so that one or more ordered lists of related biological elements and other factors affecting a disease or medical syndrome are produced as partial results, and knowledge is extracted by combining these partial results into a final result. The final result may include information on the importance of each element and its contribution to the disease or syndrome. In a variation of an exemplary embodiment of the invention, the above analysis and knowledge extraction may include treatment regimes, medicaments, and natural or chemical supplements. In addition to the above, the invention also produces associations among medical topics that could be exploited for guiding medical research.

The advantage of the present invention over other known techniques is the use of various analysis methods, each one providing a different insight or viewpoint on the same scientific data. The partial results produced by the chosen methods can provide additional knowledge missed by any single or combination of fewer methods and lead to a more accurate final result. The combination of the partial results is done in a way placing varying importance on each partial result according either to rules or learning of the algorithm from its previous applications to these or other data sets.

The invention can be embodied as a computer-implemented method, or a software program running on a computer and transforming it to a special-purpose computer configured to discover biological elements (genes, proteins, biomarkers, biomolecules, Genes, Biological Pathways and Biological functions most relevant to any medical Topic of Interest, etc.), and environmental and nutritional factors that are associated with diseases and medical syndromes, or as a microprocessor, or a computer, or a computer system, or a computational device with a single or multiple processors, or as a distributed computing system comprising the hardware resources of more than one computer. In one aspect the invention is implemented in purpose-built microprocessors, or computing systems, which are designed for optimizing the execution of the algorithms and the steps of the invention. The description of the invention is presented, for simplicity, in terms of a computer-implemented method but it is assumed to equally apply to the other forms of implementation previously mentioned.

FIG. 1 shows an exemplary computing system implementing the present invention. A user may use computer 160 or in alternative exemplary embodiments, computer 160 may be replaced by a computing device, or a server or any other type of computing system, not shown in FIG. 1. The computer 160 is connected via the Internet, or Intranet, or Cloud 150 (or via any other type of local network or local data and/or control bus) to a first database 110 holding a collection of medical data in the form of tables or files. In other embodiments a second database 120 or additional databases (not shown) may be connected. In a modification of the present embodiment, a first data file 130 and/or a second data file 140 (and/or additional data files—not shown) may be stored at a remote computer (not shown) connected to the computer 160 via any type of network 150. In a variation of the present exemplary embodiment, the data files 130, 140 may be stored in the computer 160.

Figure 2:
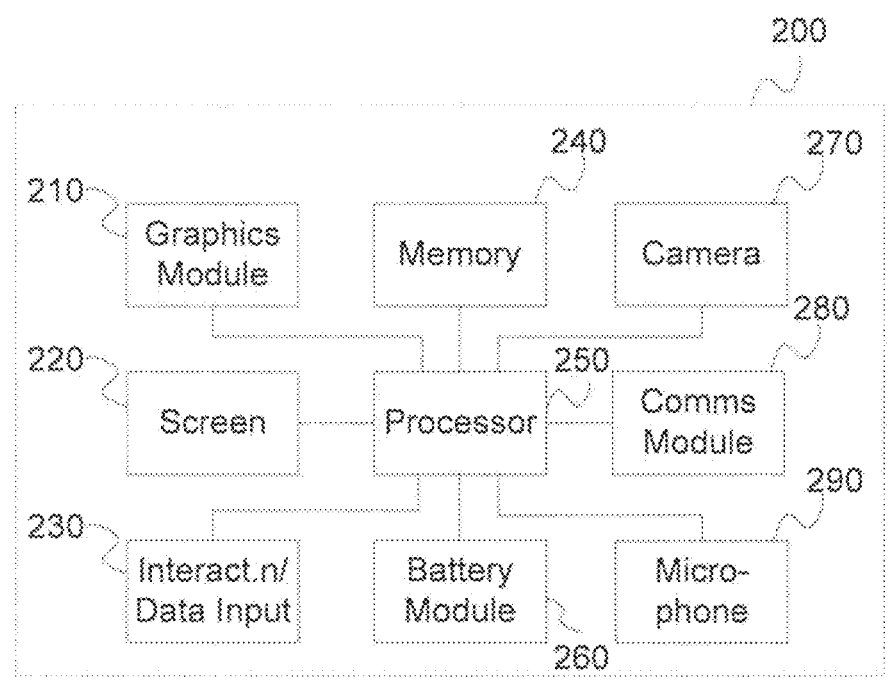
FIG. 2 shows an exemplary computer architecture used to implement the invention or parts of it.

FIG. 2 shows an exemplary computer architecture used to implement the invention or parts of it. The computer 200 comprises a Processor 250 upon which a Graphics Module 210 (in some exemplary embodiments the graphics module may be omitted), a Screen 220 (in some exemplary embodiments the screen may be omitted), an Interaction/Data Input Module 230, a Memory 240, a Battery Module 260 (in some exemplary embodiments the battery module may be omitted), a Camera 270 (in some exemplary embodiments the camera may be omitted), a Communications Module 280, and a Microphone 290 (in some exemplary embodiments the microphone may be omitted). Other elements may be included in the computer 200 in addition to or replacing those shown in FIG. 2. In alternative exemplary embodiments, additional Processors may be used on the computer 200, or in the case of a distributed system the Processor 250 may communicate with, supervise the operation of, or collaborate with the additional processors inside other computers (not shown) which are connected to the computer 200 via network 150.

Figure 3:
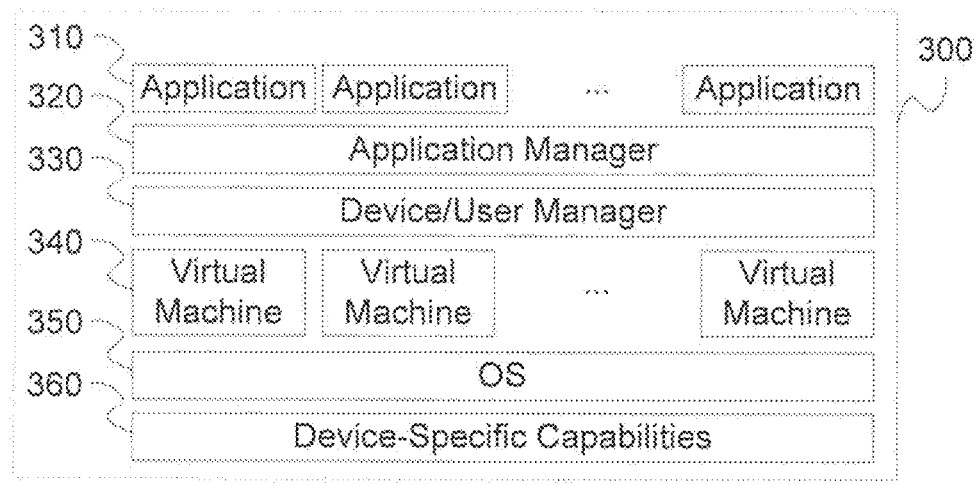
FIG. 3 shows the main Software Components of a computer or a mobile device.

FIG. 3 shows the main Software Components of a computer or a mobile device. At the lowest layer are the Device-Specific Capabilities 360, that is the device-specific commands for controlling the computer's various hardware components. Moving to higher layers lie the Operating System (OS) 350, Virtual Machines 340 (like a Java Virtual Machine), Device/User Manager 330, Application Manager 320, and at the top layer, the software Applications 310. These applications may communicate, access, manipulate and display data. These software components 300 may be implemented in any preferred programming language or in a combination of two or more programming languages.

Figure 4:
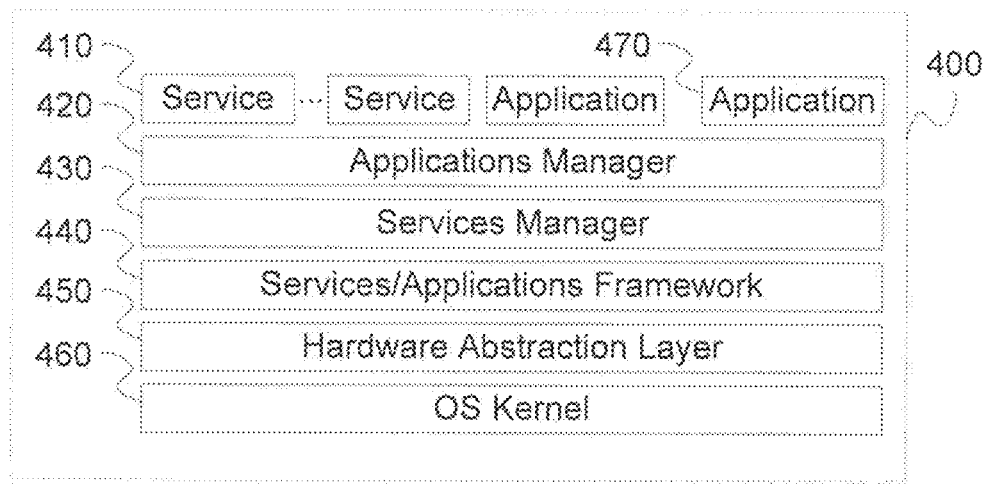
FIG. 4 shows the main Software Components of a Server.

FIG. 4 shows the main Software Components of a Server. At the lowest layer is the OS Kernel 460 followed by the Hardware Abstraction Layer 450, the Services/Applications Framework 440, the Services Manager 430, the Applications Manager 420, and the Services 410 and Applications 470. These software components 400 may be implemented in any preferred programming language or in a combination of two or more programming languages.

It is noted, that the software and hardware components shown in FIG. 3 and FIG. 4 are by means of example and other components may be present but not shown in these Figures, or some of the displayed components may be omitted or replaced with others.

The present invention may also be implemented by software running at the computer 160, or at one or more distributed computers not shown (e.g. cloud infrastructure, remote servers or other computing devices, etc.), or any combination of these. It may be implemented in any computing language, or in an abstract language (e.g. a metadata-based description which is then interpreted by a software and/or hardware component). The software running in the above mentioned hardware, effectively transforms a general-purpose or a special-purpose hardware or computer into one that is configured to specifically implement the present invention.

Figure 5:
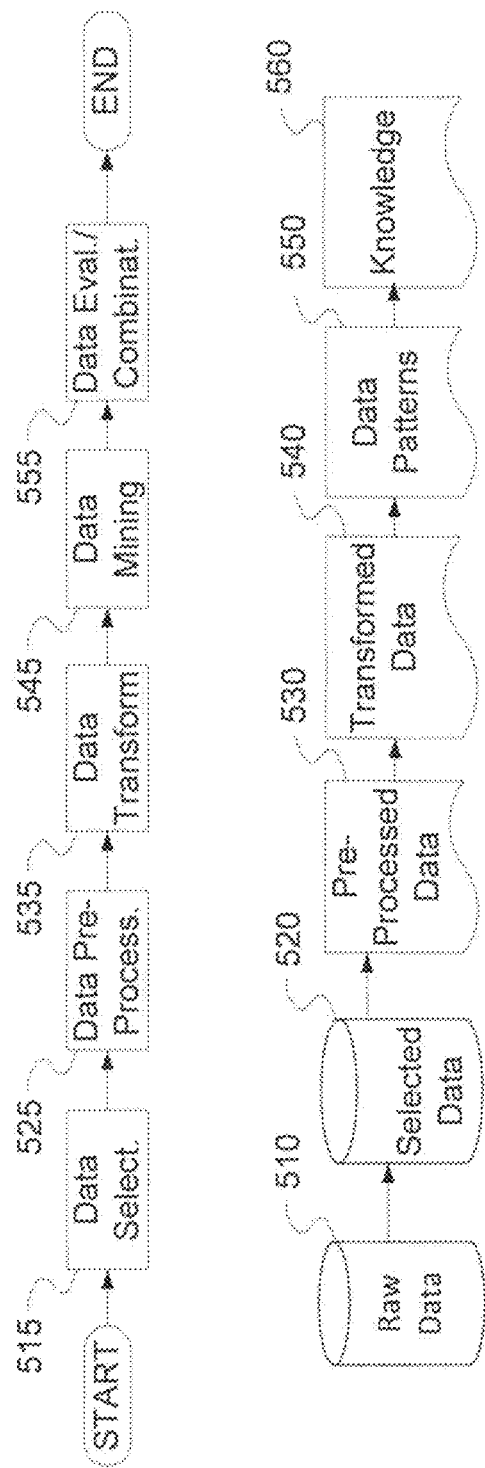
FIG. 5 illustrates the main steps in transforming raw data to knowledge.

FIG. 5 illustrates the main steps in transforming raw data to knowledge. Raw medical data 510 are accessed by the current method. These data are either stored at a remote database (e.g. PUBMED, etc.) containing large data sets from international research and publications, or at a database or any type of data file or data structure that may be stored either remotely (at a server, remote computer, the cloud, etc.) or locally at the computer 160 implementing the current invention or at one or more built-in or external memory or computer-readable medium. These data may contain any type of medical-type results, comprising, for example, drug studies, genetics studies, publications at medical journals, etc. The method continues by selecting 515 a subset 520 of the raw data 510. This selection may be made according to any relevant type of criteria. For instance, one may choose to query the database 110 (or search in the data file 130 or data structure, or memory, or computer-readable medium) for results or articles containing a gene or a disease. By means of example, querying the database 110 may be done by using any software programming language. The returned result of the database query 520 (or file or data structure search, or memory, or computer-readable medium query) is retrieved by computer 160. In a modification of this exemplary embodiment, the selected data 520 may be stored remotely at a computer or some type of storage medium which is accessible or will be made accessible to the computer 160.

The method continues by pre-processing 525 the selected data 520 to produce the preprocessed data 530. The step of preprocessing 525 may comprise one or more operations, such as normalization of the selected raw data so as to produced homogenized data which are suitable for more processing. Data normalization may include replacing all words with the same root by a single word where this word will then appear in all elements (e.g. abstracts or files) of the normalized data. For example, occurrences of the words "gene", "genes", "Gene", etc. will be replaced by the word "GENE" (i.e. a tag) which is then common across all data sets and can facilitate further processing. Other forms of pre-processing may be used. For example, synonym information such as occurrences of P450scc that are equivalent to gene CYP11A1, are normalized to become CYP11A1. The pre-processing step may also include user intervention for selecting parameters etc. or may be fully automated by reading rules and parameters from special files stored remotely or locally at the computer 160, or in a memory or computer-readable medium. It may, for example, be combined with any Natural Language Processing (NLP) or Information Extraction (IE) techniques available in literature to perform the normalization operation. In another exemplary embodiment, NLP may be replaced with Natural Language Understanding (NLU) where additional criteria and metadata may be used not simply for normalizing the data but also for more narrowly selecting data for the following processing steps. For example, searching in the scientific abstracts containing terms "Gene X" and "Disease_A", NLU may help reject those results that contain both terms but with a negation like in "there was not a statistically significant interaction between the Gene-X SNPs and DISEASE_A". NLU may also identify variations of the same meaning (for example, a gene mutation that is or is not associated with a disease or medical syndrome). The choice of NLP/NLU method is open to any such method known to any person of ordinary skill in related art. In a variation of the current exemplary embodiment, more than one NLP/NLU/pre-processing methods may be used and their partial results be combined into a single preprocessed data output 530. The method for combining such partial preprocessing results may be selected among any such method known to any person of ordinary skill in related art. By means of example and without limiting the scope of the present invention, it may include scoring and weighting, or simple merging of the discovered data tags.

The method continues by transforming 535 the preprocessed data into a transformed data 540 set which may be in a different feature space that is more suitable for data mining or any knowledge extraction technique to operate upon. The choice of transformation method is open to any relevant method from those reported in related prior art and are known to any person of ordinary skill in this art. By means of example, the frequency space may be selected for the data transformation. In alternative embodiment no transformation is made, and the method collects inherent data information (e.g. for the word tag "GENE" the inherent data information may, for example, be "noun", "singular", "occurred near another word tag", etc.).

One or more Data Mining (DM) algorithms 545 may then be applied to the transformed data 540 (in the previous alternative embodiment, the DM algorithms may use the collected inherent data information). For example one or more of the following types of algorithms may be used:

ML: (Decision Trees (DT), Rule Learning, and Instance Based Learning (IBL), such as k-Nearest Neighbors (k-NN), Genetic Algorithms (GA), Artificial Neural Networks (ANN), Random Forests (RF), and Support Vector Machines (SVM))

DM: (Anomaly detection, Association Rule Learning, Classification, Regression [e.g. Ordinary Least Squares Regression, Linear Regression, Multivariate Adaptive Regression Splines, etc.], Summarization, Bayesian Networks)

Network Analysis (NA): (Homophily, Network Closure, Centrality, Density, Distance, Tie Strength, Clustering coefficient)

Feature Selection: (Exhaustive, Best First, Simulated Annealing, Genetic Algorithm, Greedy Forward Selection, Greedy Backward Elimination, Particle Swarm Optimization, Targeted Projection Pursuit, Scatter Search, Variable Neighborhood Search, Minimum-Redundancy-Maximum-Relevance (mRMR) Feature Selection, Recursive Feature Elimination, HITON Markov Blanket)

The output of the DM algorithm(s) 545 contains one or more data patterns 550, which are evaluated and, in the case of multiple DM algorithms and results, combined into a single result 555. This evaluation and combination of data features may be done using any type of scoring-evaluation algorithm and may also include ordering of the individual and combined results. The final outcome of the invention is a list of words 560, that is, topics relevant to a disease or symptom. These topics are used to form knowledge comprising a list of relevant Genes, Biological Pathways, Medications, Vitamins, etc. relevant to a Disease, Syndrome or any other Biological Entity.

Figure 6:
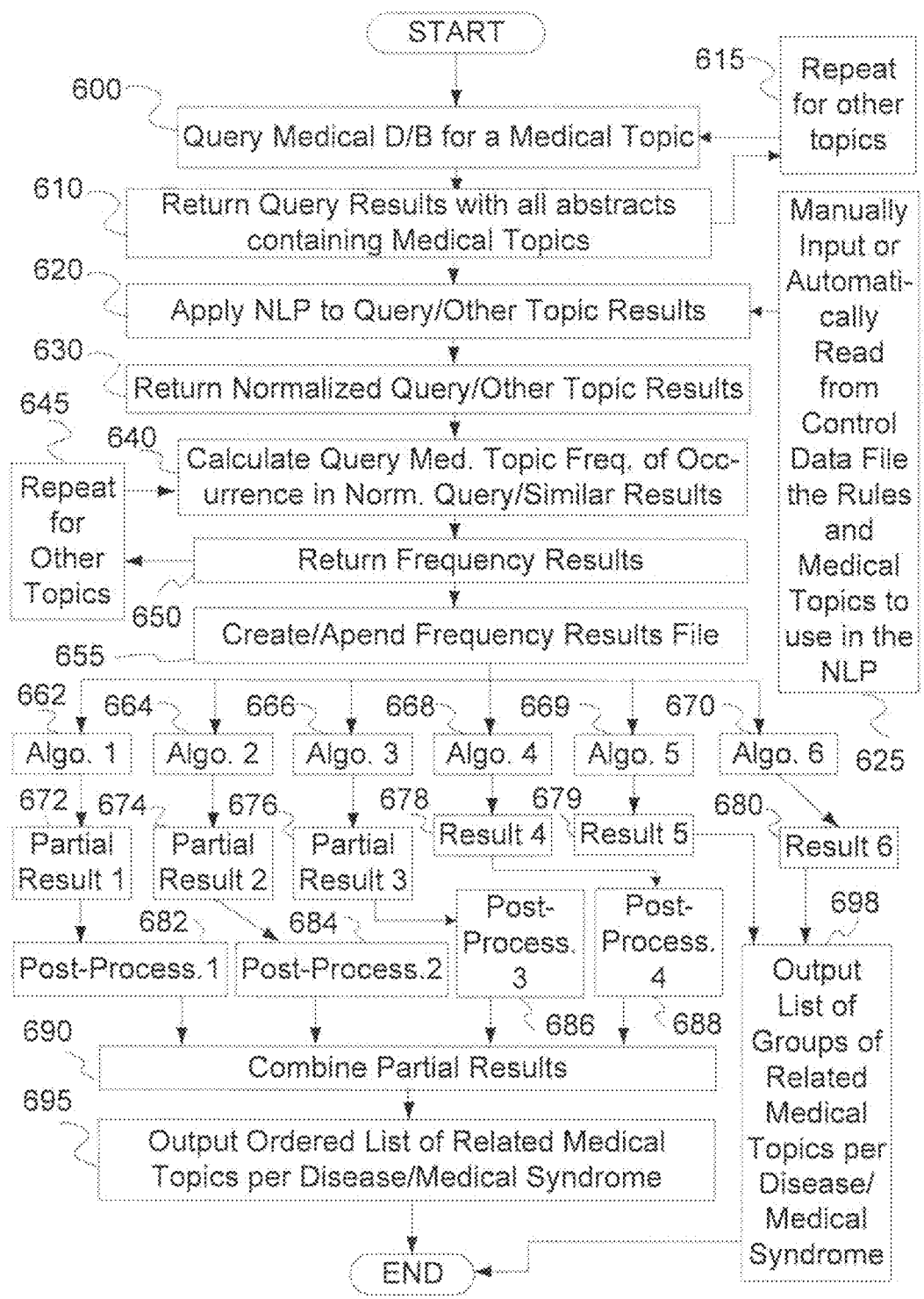
FIG. 6 frequencies.csv file containing raw frequencies of topics.

FIG. 6 shows a detailed step-by-step description of the present invention. The method starts by querying 600 a medical database for a medical term. By means of example, the PUBMED database may be queried for a disease, a medical symptom, a gene, a protein or any other medical term. Alternatively, any other public or private database may be queried, either local, remote, or distributed across more than one computers, or in a memory or in a computer-readable medium, or data files or data structures can be searched instead of or in addition to databases. In an alternative exemplary embodiment, multiple term queries may be made, e.g. queries containing at least one disease and/or at least one syndrome (or other term or factor) in the same query.

The query returns a result 610 comprising a list of occurrences of the query term or terms. This result may take the form of a vector, table, list, linked list, or file or any other type of known data structure. By means of example, let's consider querying PUBMED for "Disease A", returning a Comma-Separated Values (CSV) file named Disease_A.CSV. Other file formats could be used. Disease_A.CSV comprises a list of abstracts containing the term "Disease A" out of all the abstracts of scientific articles stored in PUBMED.

In a similar way to step 600, other queries to PUBMED may be made 615 or have been made in the past and which created a number of .CSV files, each file containing the results for a query term, e.g. Disease_B.CSV, Syndrome_1.CSV, Syndrome_2. CSV, Protein_1.CSV, etc. All these results are stored (locally, or remotely, or in the cloud, or distributed across several computers) for later use in the method of the current invention.

Each .CSV file contains a list of abstracts or full texts from scientific publications, which abstracts or full texts contain the queried term. However, there may be differences in the occurrence of queried terms and other terms across the abstracts. By means of example, we may consider the contents of P450scc.CSV, i.e. abstracts containing the term "P450scc", which represents the Cholesterol Side-Chain Cleavage Enzyme that is a mitochondrial enzyme that catalyzes conversion of cholesterol to pregnenolone. This is the first reaction in the process of steroidogenesis in all mammalian tissues that specialize in the production of various steroid hormones. The abstracts in P450scc.CSV are pieces of text in natural language:

Abstract_1: [ . . . this gene encodes the member of the cytochrome P450 superfamily of enzymes . . . . ]

Abstract_2: [ . . . the P450scc mutation, an in-frame insertion of Gly and Asp between Asp271 and Val272, was inserted into a catalytically active fusion protein of the P450scc system (H2N-P450scc-Adrenodoxin Reductase-Adrenodoxin-COOH), completely inactivating enzymatic activity . . . . ]

Abstract_3: [ . . . haploinsufficiency of P450scc causes a late-onset form of congenital lipoid adrenal hyperplasia that can be explained by the same two-hit model that has been validated for congenital lipoid adrenal hyperplasia caused by StAR deficiency . . . . ]

. . . .

Abstract_n: [ . . . because p450scc is needed for placental biosynthesis of progesterone, which is required to maintain pregnancy . . . . ]

It should be noted that use of English text is for exemplary purposes, and other languages or combinations of languages may also be used. As we note, the above abstracts, contain medical terms (such as "P450", "P450scc", "p450scc", "CYP11A1") that may have different format across the abstracts. In another example, "gene", "genes", "Gene", "P450scc", "CYP11A1", etc. may occur. These terms have the same root and/or convey identical or very closely related information. In order to facilitate further processing in the present invention, normalization is needed so that they are replaced by a uniform term, e.g. "CYP11A1", in all occurrences across all abstracts. This normalization step is achieved by a Natural Language Processing algorithm, (NLP) 620, which uses a set of rules and parameters for understanding the natural language in the abstracts and the specialized terminology they contain. The rules (and the medical terms to take into account) are selected either manually by the user of the invention or automatically 625 from a control file or other control data structure according to the needed analysis. They may include synonyms, foreign and alternative spellings, and abbreviations of the medical terms to use in the NLP and the logic to understand and extract useful information, like for instance assertion and negation which may be normalized as follows:

Original Text: " . . . Gene P450scc . . . . It was found that P450scc is related to Disease A, while Gene 2 is not reported as expressed in statistically significant results associated with Syndrome 1 . . . "

Normalized Text: " . . . CYP11A1 . . . . It was found that CYP11A1 RELATED_TO DISEASE_A, while GENE_2 NOT RELATED_TO SYNDROME_1 . . . ."

The normalized text (in capitals) is now in a format that may be used for further processing by the invention. In alternative embodiments, the NLP step 620 uses a list of medical topics which are then matched in the abstracts to understand the meaning of the text. These topics may take the form of a lexicon and/or thesaurus, which may contain synonyms, foreign language synonyms, multi-word descriptions of the said term, etc. and which may be created during previous applications of the invention, may be imported from external sources, or may be manually edited by the user of the current method. According to this exemplary use of the invention, in the NLP step, the algorithm may check a number of consecutive words for identifying meanings like assertion or negation or other. Consider the following sequence of words in an abstract:

. . . Word 1 . . . Word 2 . . . Word 3 . . . Word 4 . . . Word 5 . . . Word 6 . . . Word 13 . . . .

" . . . IL-2-330A>C was found to have a statistically significant interaction with Chronic Fatigue Syndrome . . . "

The algorithm may set an analysis window of size x, where x may be set equal to three consecutive words. This window is sliding over the above word sequence, each time examining x consecutive words (n-gram), e.g. three words in the following example:

Window 1: [Word 1 . . . Word 2 . . . Word 3]
" . . . IL-2-330A>C . . . was . . . found . . . ."
Window 2: [Word 2 . . . Word 3 . . . Word 4]
" . . . was . . . found . . . to . . . ."
Window 3: [Word 3 . . . Word 4 . . . Word 5]
" . . . found . . . TO . . . HAVE . . . ."

. . . .

Window 8: [Word 8 . . . Word 9 . . . Word 10]
" . . . significant . . . INTERACTION . . . WITH . . . ."
Window 9: [Word 9 . . . Word 10 . . . Word 11]
" . . . CHRONIC . . . FATIGUE . . . SYNDROME . . . ."

In the above example, the NLP algorithm 620 identified in the normalized abstract's text the medical terms IL-2-330A>C, INTERACTION WITH, CHRONIC FATIGUE SYNDROME and the logical terms TO HAVE. Based on its rules, it extracts the following information:

IL-2 RELATED_TO CFS

In a variation of the above exemplary embodiment, the text is grammatically and syntactically analyzed by any known method for identifying classes of words (verbs, nouns, etc.), logical operations (e.g. negation, addition, etc.), number (e.g. singular or plural), condition (e.g. a prerequisite), etc. that are used into understanding the content and context of the information conveyed by the text.

In another exemplary embodiment of the NLP step 620, we assume we are searching the scientific abstracts for a gene. Genes may be referred to in a number of ways, e.g. "rs" followed by a number ("rs104122"), or a combination of capital letters and numbers ("CYP11A1"). Using this a priori knowledge we can configure the NLP algorithm to search and match any of these formats and identify and normalize genes in an abstract text. Similar knowledge can be used in searching other biological and medical terms.

The rules, parameters and methods used in the NLP step 620 can be selected among the available NLP, IE, Entity Deletion, and statistical techniques reported in literature and are not limited to any particular technique, implementation or the above example. For instance, other rules are used when searching for genes (as in the above exemplary embodiment) and others when searching for proteins or other biological elements or nutritional or environmental factors. In a variation of the above exemplary embodiment, the set of rules for identifying the elements and factors may search at once for genes, proteins, biomarkers, humidity level, temperature, vitamins, minerals etc. as these may affect a disease or a medical condition we are interested in identifying its influence factors.

The output 630 of the NLP step 620 may be stored in a file, database or any other data structure. By means of example let's consider it is stored in file P450scc_NLP.CSV for the case where the queried topic is P450scc. Similar files may exist from previous applications of the invention for other medical terms.

The method continuous by calculating the frequency of occurrence of the normalized medical topic in the previous file 640, as well as, in all other stored .CSV files, previously created.

The frequency of occurrence of the normalized medical topics are calculated by one of the following ways:

a) counting the number of occurrences of the topic in a .CSV file and dividing it by the number of lines in each .CSV file b) counting the number of occurrences of the topic in a .CSV file and dividing it by the number of words in the .CSV file, excluding stop words (i.e. frequent words such as "to", "and", "is", "at", "over", "one", "two", "three" etc.)

c) counting the number of occurrences of the topic in a .CSV file and dividing it by the number of abstracts in each .CSV file For example for medical term "histidine" (i.e. an α-amino acid that is used in the biosynthesis of proteins and which is abbreviated as His or H;) the result of the NLP step is stored in file histidine.CSV and the following frequencies (see Table 1) are calculated for the histidine.CSV and all other available .CSV files for other medical terms. In an exemplary implementation of this method, the frequency of occurrence column results are transformed into a row which is added to the FREQUENCIES.CSV file.

TABLE 1

Frequency of Occurrence of Medical Term "histidine" in .CSV files

| FILE | FREQUENCY OF OCCURENCE |
|---|---|
| histidine.csv | 100.00% |
| hnmt.csv | 18.63% |
| heme.csv | 5.06% |
| heme_biosynthesis.csv | 4.87% |
| glutamine.csv | 4.65% |
| ... | ... |

"histidine" is found in all abstracts (100.00%) in the histidine.csv file which contains the results for query "histidine" in PUBMED.

In 18.63% of the abstracts in file hnmt.csv containing the results of query "hnmt", in 5.06% of the abstracts in heme.csv, in 4.87% in heme_biosynthesis.csv, in 4.65% in glutamine.csv, an so on.

These results may be returned and stored 650 in any type of data structure, or file or database. By means of example, we assume they are stored in the FREQUENCIES.CSV file using the following rows:
<l_histidine>,<hnmt>,<heme>,<heme_biosynthesis> . . . .
0.7829,0.1863,0.506,0.487 . . . .

In an alternative exemplary embodiment of the method, the frequency calculation step 640 may be repeated 645 for other medical topics. In this case the FREQUENCIES.CSV file may be appended 655 or replaced by a file containing the results of a complex query which comprises two or more medical term. Additional rows would then be added to contain the results for the other medical terms, or a single row could contain the result for all abstracts containing all the medical terms in the query.

Following the previous steps, the frequency data are fed to at least one algorithm to analyze them and extract knowledge out of them. A number of algorithms are used to analyze the same data and derive results based on an analysis placing different emphasis on a set of features.

These algorithms may produce results that can be grouped with results from other algorithms (or in some cases with results from algorithms of the same category) and ordered according to some criterion) or produce individual results not suitable for combination with results from other algorithms. These individual results may be exploited as suggestions for use in further medical research (e.g. new and unexpected medical topics that appear to be related to a disease). These algorithms may operate on the calculated (raw or stateless) frequency data 655, in stated frequency data where the original frequencies 655 are converted into a True or a False State using a Threshold Value or operate on input data where certain feature original frequencies are kept and features that represent a symptom, are grouped onto a single "symptom" feature if a threshold frequency value is exceeded.

In the following exemplary analysis the following terms have the following meanings:
NRF1 is the Nominal Response Feature 1 (T/F values) that represents any Medical Topic such as disease, individual Symptom (not grouped Symptoms), Gene, Pathway etc.
NRF2 is the Nominal Response Feature 2 (T/F values) that represents a group of Symptoms that are usually present to a Syndrome or Disease.
ASSOC is any Associations Rule Algorithm
NA is any Network Analysis Algorithm (Degree, Authority, Hub, etc.)
CLUS is any Cluster Analysis algorithm
CL1 is any Classification Analysis Algorithm (or other ML Algorithm), using Numeric Features Input, Nominal Response Feature NRF1 or NRF2
CL2 is any Classification Analysis Algorithm (or other ML Algorithm), using Nominal (T/F) Input, Nominal Response Feature NRF1 or NRF2
CD is any Community Detection Algorithm (e.g. Cluster Walktrap)
HS1 is any HOTSPOT Algorithm, using Numeric Input Features, Numeric Response Feature
HS2 is any HOTSPOT Algorithm, using Nominal (T/F) Input Features, any Nominal Response feature NRF1 or NRF2
FS1 is any Feature Selection Algorithm, using Numeric Inputs, Numeric Response Feature
FS2 is any Feature Selection Algorithm, using Nominal Inputs, Nominal Response NRF1 or NRF2
FS3 is any Feature Selection Algorithm, using Numeric Inputs, Nominal Response Feature NRF1 or NRF2

Figure 9:
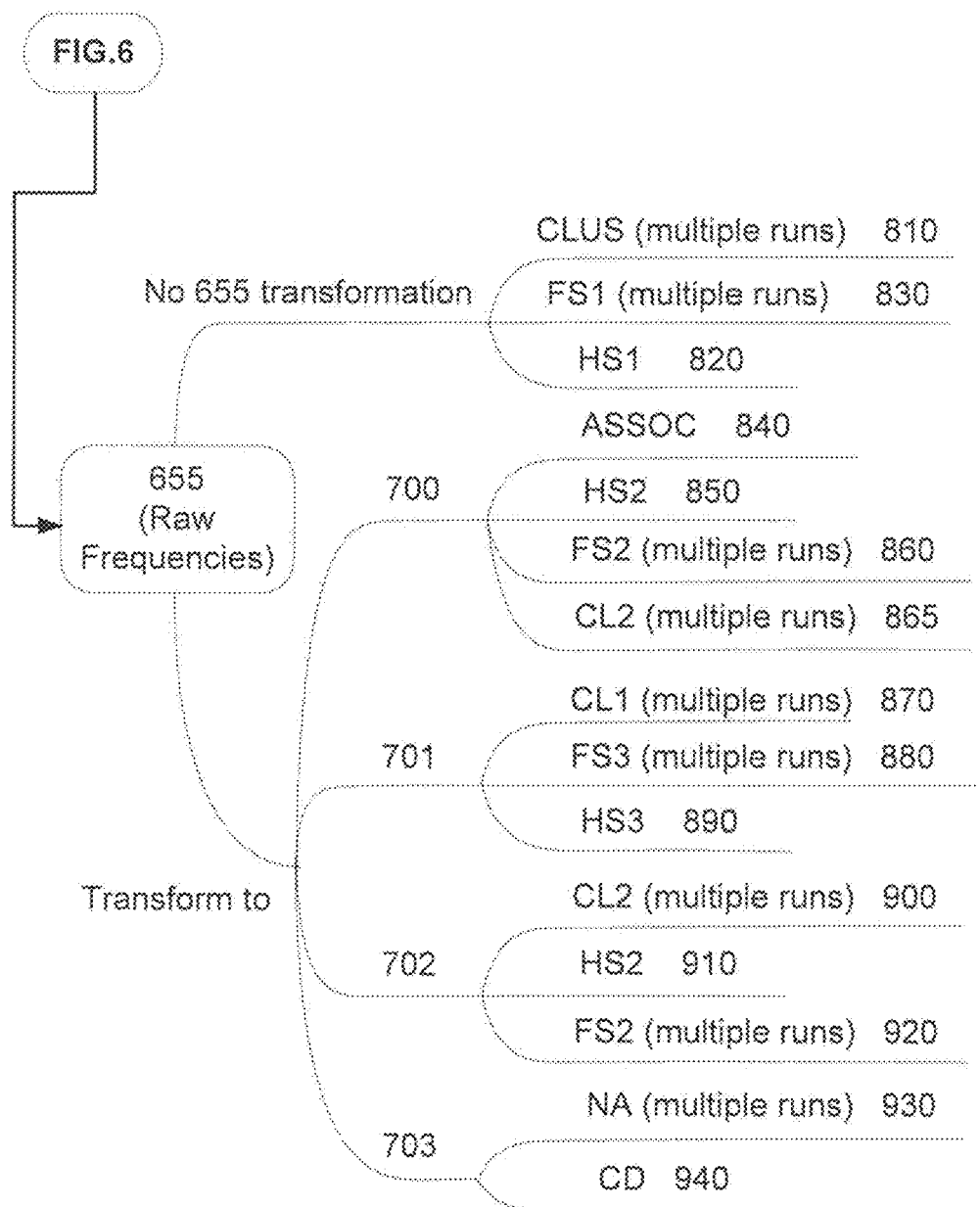
FIG. 9 shows how frequency files are analyzed and how results from individual algorithms are combined.

FIG. 9 shows how frequency files are analyzed and how results from individual algorithms are combined. The analysis starts with the calculated frequencies file 655. This file may either be transformed into a new dataset 700 which contains T/F values instead of frequencies.

If a frequency exceeds a threshold value T1 then "True" is inserted otherwise "False" is inserted for every cell of the frequencies file.

File 655 may be also transformed to dataset 701 where feature columns containing symptoms (e.g. insomnia.csv, orthostatic intolerance.csv, etc.) are grouped into a single feature named "Symptom" set to "True" if any symptom frequency value across each row exceeds a threshold value T2, otherwise it is set to "False". File 701 also contains the original numerical frequencies alongside the Nominal Response Feature NRF2 which—as described—groups all symptoms to a single feature.

File 655 may be further transformed to file 702 where we have a number of features that contain T/F values (according to threshold T1, as in the case of file 700) and also a feature called "Symptom" that contains a value of T/F values as in the case of file 701. File 702 therefore contains the T/F frequencies as input features alongside Nominal Response Feature NRF2.

File 655 may be also transformed to a file 703 which contains pairs of features having a Pearson correlation exceeding Threshold T3.

The method then proceeds with various types of analysis according to the input files 655,700,701,702,703 as follows:
file 655 may be analyzed by any Clustering Algorithm CLUS to create output 810. 810 contains a number of associated topics that were found during the clustering process. 810 cannot be grouped with any other results output.

file 655 may also be analyzed by HS1 HOTSPOT algorithm to create output 820 file 655 may also be analyzed by any number of FS1 Feature Selection Algorithm to create results output 830 file 700 may be analyzed by any number of Association Rule Learning Algorithm ASSOC to create output 840 file 700 may be also analyzed by HS2 HOTSPOT algorithm to create output results 850 file 700 may be also analyzed by any number of FS2 Feature Selection algorithm to create results 860 file 700 may be also analyzed by any number of CL2 Classification Analysis algorithm to create results 865 file 701 may be analyzed by any number of CL1 Classification Analysis Algorithm to create results output 870 file 701 may be also analyzed by any number of FS3 Feature Selection algorithm to create results output 880 file 701 may be also be analyzed by HS3 HOTSPOT algorithm to create results 890 file 702 may be analyzed by any number of CL2 Classification Analysis Algorithm to create results output 900 file 702 may be also analyzed by any HS2 HOTSPOT Algorithm to create results output 910 file 702 may be also analyzed by any number of FS2 Algorithm to create output 920 file 703 may be analyzed by any number of NA Network Analysis algorithms to create output 930 file 703 may be also analyzed by any number of Community Detection Algorithm to create output 940

The resulting outputs may be combined as follows:

Group 1: may combine results 930 (multiple runs of different algorithms of the same category—results are optionally considered), 870 (multiple runs of different algorithms of the same category), 880 (multiple runs of different algorithms of the same category), 890 with the aim to identify the most promising Medical topics relevant to a group of Symptoms, Disease or Syndrome.

Group 2: may combine results 930 (multiple runs of different algorithms of the same category—results are optionally considered), 900 (multiple runs of different algorithms of the same category), 910, 920 (multiple runs of different algorithms of the same category) with the aim to identify most promising Medical topics relevant to a number of Symptoms/Disease or Syndrome. The difference with results of Group 1, is that the input features in this Group are T/F Values as opposed to numeric input frequencies that Group 1 uses Group 3: may combine results 830 (multiple runs of different algorithms of the same category). This group combines results from any number of FS1 Algorithm that output results 830 using 655 as input data Group 4: may combine results 850,860 (multiple runs of different algorithms of the same category), 865 (multiple runs of different algorithms of the same category). This group uses 700 as input data and algorithms that use NRF1 as Response feature which means that we do not investigate for grouped Symptoms but we investigate at any Medical Topic using a T/F Representation Results 810, 820, 840, 930, 940 have an exploratory nature which means that there is no specific symptom, syndrome or disease being investigated. Note that 930 may also be used for non-exploratory purposes when combined with other results (in Groups 1 and 2, 930 results may be optionally considered).

Algorithms NA, FS1, FS2, FS3, CL1, CL2 may be run using different algorithms respectively and thus create individual grouped results. These grouped results of the individual algorithm runs may be further combined with other algorithms.

As an example we may use the same input data to:
analyze it using a CL1 Algorithm to create output1
analyze it using a second CL1 Algorithm to create output2
analyze it using a third CL1 Algorithm to create output3

Output1, output2 and output3 may be combined into a single results file output4 (grouping of results happens as previously described).

Output4 may then be combined with other analysis outputs to create a single results file (e.g. overall result from Group1).

In the present exemplary embodiment, the frequency data 655 are analyzed with up to six different categories of algorithms 662, 664, 666, 668, 669, 670, and from each category more than one algorithm may be used. In variations of this exemplary embodiment, any number of algorithm categories may be used.

Referring to the exemplary embodiment of FIG. 6, the method uses a first algorithm which is selected among any known ML algorithm 662, a second algorithm selected among any known NA algorithm 664, a third algorithm selected among any Feature Selection algorithm 666, a fourth algorithm selected among any variation of the HOTSPOT algorithm 668, a fifth algorithm selected among any Association Rule Learning algorithm 669, and a sixth algorithm selected among any Clustering algorithm 670. The first four algorithms 662, 664, 666, 668 produce partial results 672, 674, 676, 678 which effectively analyze the same data using different techniques and metrics and give different emphasis to the ordering of the various factors influencing a target medical term, e.g. different ordering and importance to the genes, enzymes, etc. affecting a disease and/or medical syndromes. There is, however, a NA algorithm, the Community Detection algorithm, which identifies clusters of medical topics and which does not produce ranked results (refer to Group2 previously discussed). The individual partial results 672, 674, 676, 678 may equally be used for exploring new medical elements instead of only finding their importance and having them ordered differently, i.e. been assigned different importance, or grouped according to similarity. In particular ML algorithms 662 can be combined with the HOTSPOT algorithm 668 and FS Algorithms 666, while NA algorithms 664 can be combined with ML algorithms 662, FS Algorithms 666 and HOTSPOT Algorithm 668 only when the NA algorithms are used to produce results with central topics. If the NA algorithms 664 are used to produce results with groups of topics then these results cannot be combined with results from other algorithm categories.

The fifth, and sixth algorithms 669, 670 work differently than 662, 666, 668 since no target topic is considered in these algorithms. They produce their results 679, and 680 which are not combined together and which may be used for supporting further medical research. Results 679, 680 are output 698 as lists of biological topics and/or groups of symptoms. In particular, the HOTSPOT algorithm 668 is used for classification of the frequency data 650 and normalizing results from other methods when combined with them. When fed with stateless frequency data and grouped symptoms, the HOTSPOT algorithm 668 produces results that can be grouped with the results of ML algorithms 662, FS Algorithms 666 and NA algorithms 664. To assess the performance of HOTSPOT algorithm 668 we rank the results, using the "lift" metric. However, when fed with stateless frequency data and ungrouped symptoms, the HOTSPOT algorithm 668 produces results that cannot be combined with results from other algorithms but can be used as terms for further exploratory medical research. Clustering algorithms 670 operate with stateless frequency data and no grouped symptoms as input and produce results 680 which cannot be grouped with the results of other algorithm categories but which can be used for exploratory medical research.

Any type of machine learning algorithm 662 may be used in order to identify, e.g. the genes and other medical terms associated with a disease or syndrome. By means of example, the following algorithms may be considered: Decision Trees, Rule Learning, k-Nearest Neighbors, Artificial Neural Networks, Random Forests, Support Vector Machines, Stochastic Gradient Descent, AdaBoost, and Singular Value Decomposition. The output of the ML step 662 is an ordered list of features (i.e. medical terms) associated with and influencing the target disease, symptom, or syndrome.

The NA Algorithm 664 starts by creating a correlation matrix from the frequencies of all medical terms using Pearson's Product Moment Correlation (shown in Table 2), or in alternative embodiments any other correlation measure known in prior art.

TABLE 2

Pearson's Product Moment Correlation Matrix

| Row ID | three_betahsd | three_m . . . | fiv_ala | five_ht2 | five_htp | five_al . . . | five_m . . . |
|---|---|---|---|---|---|---|---|
| three_betahsd | 1 | 0.016 | 0.075 | 0.007 | 0.017 | 0.042 | 0.019 |
| three_methylcrotonyl_c . . . | 0.016 | 1 | 0.051 | −0.006 | 0.003 | 0.001 | 0.017 |
| five_ala | 0.075 | 0.051 | 1 | 0.006 | 0.017 | 0.114 | 0.058 |
| five_ht2 | 0.007 | −0.006 | 0.006 | 1 | 0.504 | 0.017 | 0.031 |
| five_htp | 0.017 | 0.003 | 0.017 | 0.504 | 1 | 0.032 | 0.042 |
| five_alphareductase | 0.442 | 0.001 | 0.114 | 0.017 | 0.032 | 1 | 0.034 |
| five_mthf | 0.019 | 0.017 | 0.058 | 0.031 | 0.042 | 0.034 | 1 |
| abc_transporter | 0.041 | 0.019 | 0.106 | 0.001 | 0.002 | 0.067 | 0.028 |
| acetaldehyde | 0.056 | 0.042 | 0.105 | 0.012 | 0.027 | 0.047 | 0.04 |
| acetyl_coa | 0.086 | 0.231 | 0.141 | 0.01 | 0.023 | 0.062 | 0.068 |
| acetyl_coa_carboxylase | 0.072 | 0.198 | 0.107 | 0.004 | 0.011 | 0.053 | 0.051 |
| acetylation | 0.049 | 0.02 | 0.106 | 0.005 | 0.008 | 0.088 | 0.059 |
| acetylcholine | 0.014 | 0.006 | 0.028 | 0.079 | 0.081 | 0.022 | 0.044 |
| acetylcholinesterase | 0.012 | 0.004 | 0.027 | 0.023 | 0.027 | 0.013 | 0.018 |
| acyl_coa | 0.099 | 0.232 | 0.146 | 0.006 | 0.018 | 0.058 | 0.071 |
| adhd | −0.001 | 0.002 | 0.008 | 0.045 | 0.059 | 0.006 | 0.012 |
| adrenal_hyperplasia | 0.238 | 0.009 | 0.036 | 0.009 | 0.024 | 0.168 | 0.012 |
| adrenal_insufficiency | 0.079 | 0.009 | 0.027 | 0.005 | 0.026 | 0.058 | 0.014 |
| adrenergic_receptor | 0.024 | 0.003 | 0.023 | 0.078 | 0.073 | 0.037 | 0.025 |
| adanced_glycation_end | 0.032 | 0.014 | 0.055 | 0.008 | 0.005 | 0.027 | 0.053 |
| ae2 | 0.044 | 0.02 | 0.055 | 0.007 | 0.006 | 0.035 | 0.019 |
| akr1d1 | 0.24 | 0.028 | 0.135 | 0.025 | 0.04 | 0.228 | 0.055 |
| ala_synthase | 0.086 | 0.07 | 0.4 | 0.002 | 0.009 | 0.047 | 0.027 |
| allopregnanolone | 0.326 | 0.013 | 0.037 | 0.04 | 0.058 | 0.223 | 0.016 |

| Row ID | abc_tr . . . | acetal . . . | acetyl . . . | acetyl . . . | acetyl . . . |
|---|---|---|---|---|---|
| three_betahsd | 0.041 | 0.056 | 0.086 | 0.072 | 0.049 |
| three_methylcrotonyl_c . . . | 0.019 | 0.042 | 0.231 | 0.198 | 2 |
| five_ala | 0.106 | 0.105 | 0.141 | 0.107 | 0.106 |
| five_ht2 | 0.001 | 0.012 | 0.01 | 0.004 | 0.005 |
| five_htp | 0.002 | 0.027 | 0.023 | 0.011 | 0.008 |
| five_alphareductase | 0.067 | 0.047 | 0.062 | 0.053 | 0.088 |
| five_mthf | 0.028 | 0.04 | 0.068 | 0.051 | 0.059 |
| abc_transporter | 1 | 0.043 | 0.076 | 0.063 | 0.074 |
| acetaldehyde | 0.043 | 1 | 0.166 | 0.113 | 0.057 |
| acetyl_coa | 0.076 | 0.166 | 1 | 0.929 | 0.182 |
| acetyl_coa_carboxylase | 0.063 | 0.113 | 0.929 | 1 | 0.104 |
| acetylation | 0.074 | 0.057 | 0.182 | 0.104 | 1 |
| acetylcholine | 0.015 | 0.021 | 0.054 | 0.028 | 0.028 |
| acetylcholinesterase | 0.012 | 0.023 | 0.042 | 0.021 | 0.017 |
| acyl_coa | 0.08 | 0.164 | 0.685 | 0.548 | 0.113 |
| adhd | −0.002 | 0.007 | 0.008 | 0.006 | −0.001 |
| adrenal_hyperplasia | 0.013 | 0.019 | 0.029 | 0.028 | 0.019 |
| adrenal_insufficiency | 0.01 | 0.016 | 0.041 | 0.042 | 0.016 |
| adrenergic_receptor | 0.013 | 0.021 | 0.052 | 0.053 | 0.027 |
| adanced_glycation_end | 0.032 | 0.054 | 0.113 | 0.106 | 0.062 |
| ae2 | 0.043 | 0.032 | 0.061 | 0.06 | 0.045 |
| akr1d1 | 0.068 | 0.093 | 0.153 | 0.127 | 0.067 |
| ala_synthase | 0.059 | 0.077 | 0.14 | 0.113 | 0.05 |
| allopregnanolone | 0.01 | 0.026 | 0.038 | 0.025 | 0.018 |

The algorithm then selects pairs of medical terms having correlation larger than a threshold T2 (e.g. >0.5 in an exemplary embodiment) (shown in Table 3).

TABLE 3

Correlation Pairs having Pearson correlation >T2

| Row ID | node1 | node2 |
|---|---|---|
| 0 | ndufs7 | coenzymeq10 |
| 1 | atf4 | atf6 |
| 2 | steatohepatitis | lxr |
| 3 | oxidation | redox-cofactor |
| 4 | glycerylphosphorylcholine | phospholipid_human |
| 5 | paps | phosphosulfate |
| 6 | p450oxidoreductase | p450 |
| 7 | urea_cycle | amoebic_liver |
| 8 | oxidation | steatohepatitis |
| 9 | oxidative_phosphorylation | mitochondria_human |
| 10 | flavoprotein | nadh_dehydrogenase |
| 11 | ero1 | oxidative_protein_fol . . . |
| 12 | flavoprotein | redox-cofactor |
| 13 | tnf_alpha | pyrogen |
| 14 | acetyl_coa | coa |
| 15 | al_10 | inflammatory_cytokines |
| 16 | heme_biosynthesis | heme |
| 17 | phospholipid_human | cardiolipin |
| 18 | oxidation | amoebic_liver |

As an example let's look at the first two rows:
ndufs7,coenzymeq10
atf4,atf6 ndufs7 and conzymeq10 were found to have a Pearson's Product Moment Correlation coefficient greater than 0.5. The same applies for atf4 and atf6 (shown in row 1) and the process continues for all pairs on the correlation matrix.

Then the NA calculates metrics such as Degree and Authority of each node using the processed data shown at Table 3. For example, the results for the "Degree" metric are calculated and shown below:

topic1: 15
topic2: 12
topic3: 10
topic4: 3

As a result, the NA finds important Medical Topics and groups of Associated Topics. However, Symptoms are not grouped prior to the Network Analysis. NA, therefore, shows topics that are central (i.e. important) to the data being presented. Out of the pairs shown in Table 3, a Graph is constructed. In an alternative exemplary embodiment, the calculated metrics are used as weights to create a weighted graph, i.e. a graph where the edges connecting its nodes are as long (or strong, or bold, or carry a number equal to their assigned weight) as their associated weights.

In an alternative exemplary embodiment of the NA Algorithm, any Community Detection Algorithm can be used to identify Groups of Associated Topics that may be used for further Medical Research. Results of this analysis cannot be combined with any, other results of any other analysis method.

Figure 7:
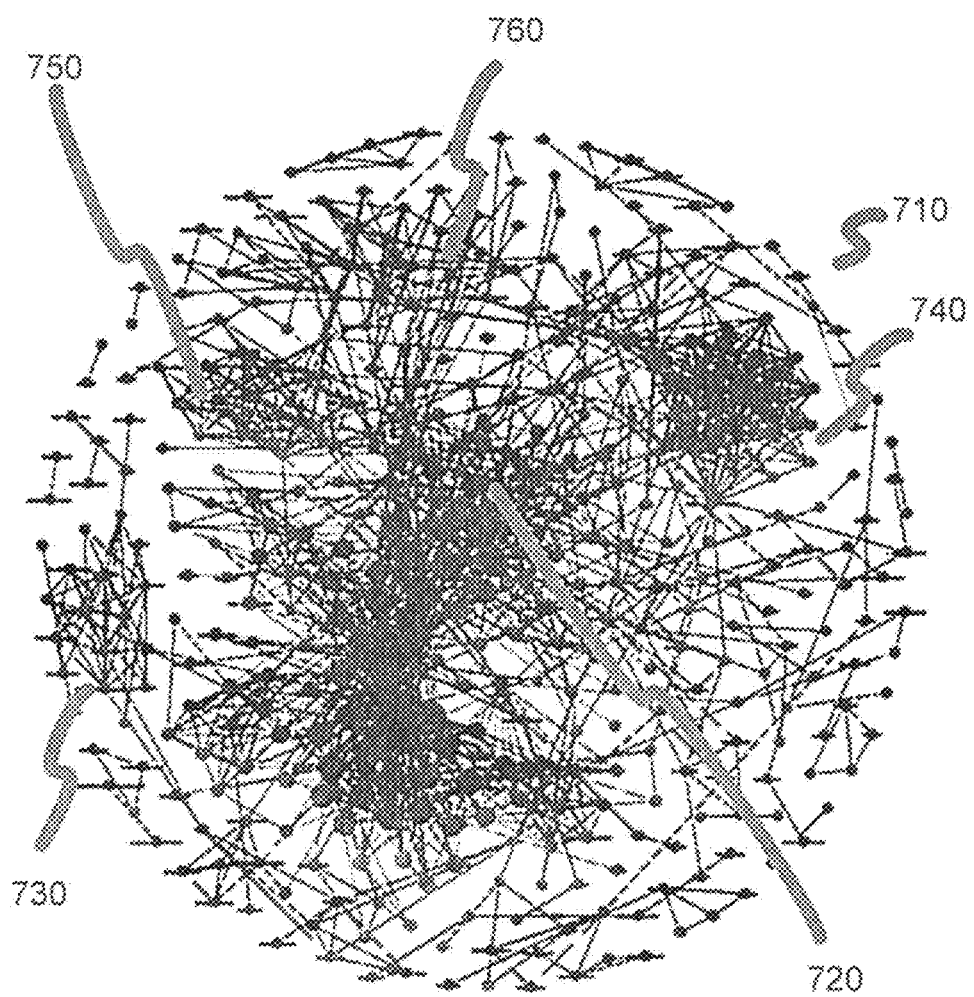
FIG. 7 shows an exemplary Graph.

FIG. 7 shows an exemplary Graph. It shows the entire graph 710 comprising clusters 710-760 of medical terms, where each cluster has some common feature like direct connections between its topics, or some other metric.

Figure 8:
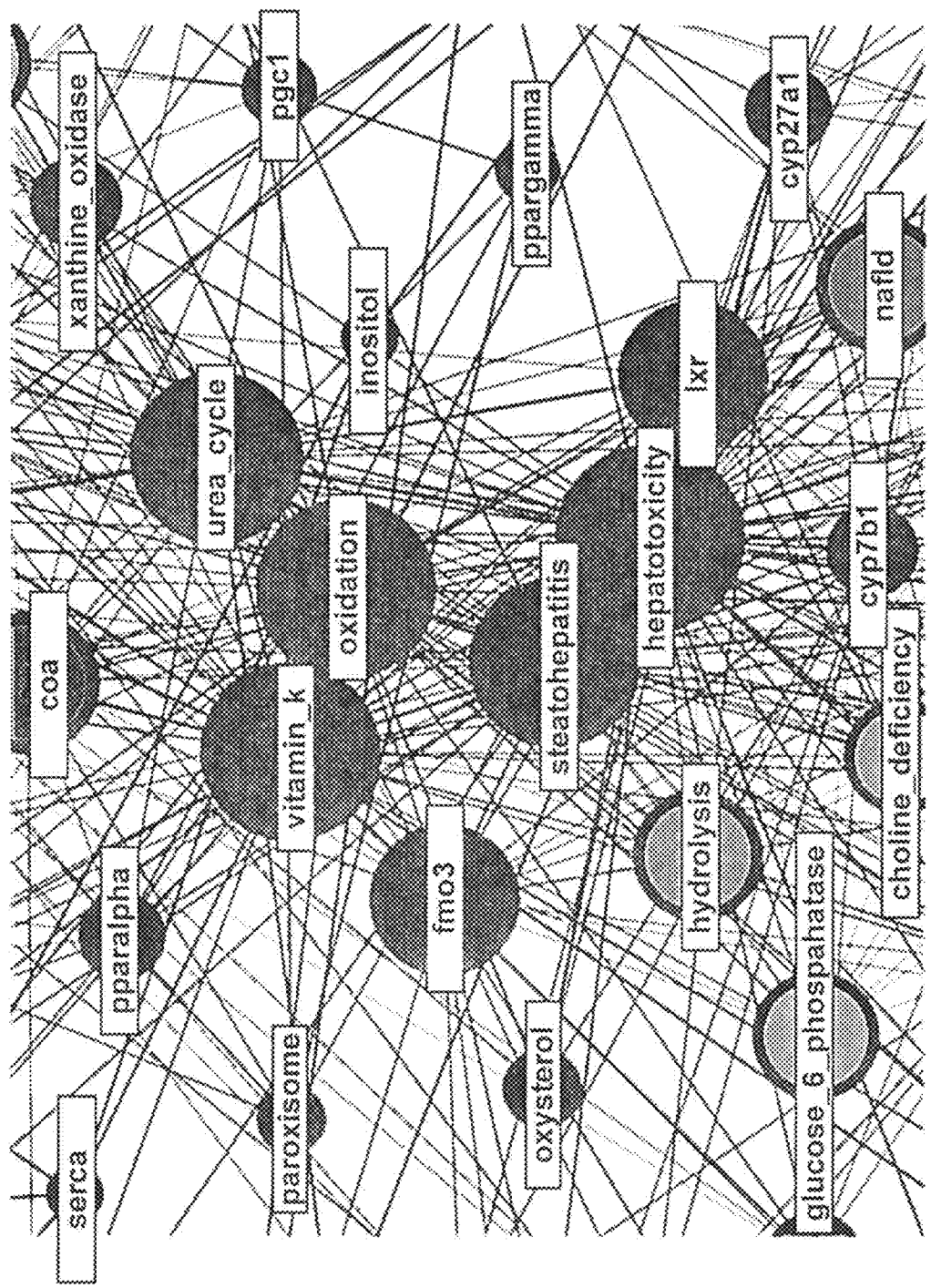
FIG. 8 shows an expanded graph view of an exemplary cluster.

FIG. 8 shows an expanded graph view of an exemplary cluster. It contains the central elements of the cluster 720 of FIG. 7 and their connections. This exemplary cluster contains among other topics, "oxidation", "vitamin_k", "urea_cycle", "fmo3", "hydrolysis" and others.

In an alternative embodiment, the graph of FIG. 7 and FIG. 8 may be directional and/or weighted and therefore convey more information on the connections, i.e. the relationship between the elements represented by its nodes.

The NA algorithm 664 continues with the calculation of metrics for the elements of the graph of FIG. 7 to identify medical topics that have a central role to the subject of research. Any type of metric can be used; by means of example and under no way limiting the present invention, the Authority and Degree metrics can be used.

As an example, if ATF6, NDUFS7, and BILE_ACIDS are found having a large Degree NA Metric, then we may conclude that these terms may be central to the research subjects we are interested in (i.e. diseases or syndromes). The output 674 is an ordered list of these terms.

TABLE 4

Weighted Degree measure for the graph of FIG. 7

| Label | Inerval | Weighted Degree |
|---|---|---|
| hepatotoxicity | | 51.0 |
| nad | | 49.0 |
| tocotrienol | | 46.0 |
| oxidation | | 44.0 |
| steatohepatitis | | 41.0 |
| vitamin_k | | 40.0 |
| urea_cycle | | 36.0 |
| ginkgo | | 36.0 |
| udpgluc | | 36.0 |
| coenzymeq10 | | 35.0 |
| cholestasis | | 35.0 |
| coa | | 34.0 |
| flavoprotein | | 33.0 |
| catalase | | 33.0 |
| quinone_reductase | | 32.0 |
| fmo3 | | 32.0 |
| cofactor | | 31.0 |
| lxr | | 30.0 |
| liver_injury | | 30.0 |
| amoebic_liver | | 28.0 |
| oxidative_stress_protection | | 28.0 |
| liver_regeneration | | 27.0 |
| glycoproteins | | 26.0 |
| hepatocytes | | 25.0 |
| pyrogen | | 24.0 |

We may consider another example where the graph of FIG. 7 is used to compute a Weighted Degree of all nodes (medical topics) of a graph that contains topics possibly related with the Chronic Fatigue Syndrome. As shown in Table 4, the "hepatotoxicity" node has the highest weighted degree score (=51) followed by nad, tocotrienol, oxidation, Vitamin K, etc.

These results may be transformed through normalization (essentially we see the same ranking of features as created by DM and Feature Selection Algorithms) and thus combined with other DM/Feature Selection/HOTSPOT outputs to a final result.

The Feature Selection Algorithm 666 selects and ranks features relevant to a Classification problem (or in a variation of the current exemplary embodiment of the invention, it creates a dataset of fewer features without looking at the Classification Label). In other words it reduces the dimensionality of the original data (e.g. Principal Components Analysis). By means of example, any of the following Feature Selection Algorithms may be used: Stepwise Forward Selection, Stepwise Backward Elimination, Combination of Forward Selection and Backward Elimination, Algorithm Wrapper Methods, Principal Components Analysis, Wavelet Transforms, Filtering of Low Variance features, Concept Hierarchy Generation, L1-based Feature Selection, and Randomized Sparse Models.

In an exemplary embodiment, the calculated frequency table (Table 1) is converted into a new table (T/F Table 5) where frequencies are replaced by "T" for "True" and "F" for "False" (file 700). This frequency table (Table 1) is an exemplary visualization of the calculated topic frequencies stored in the present example in the frequencies.csv file. Other exemplary representations and visualizations are possible. If any cell on the frequency table is larger than a given threshold frequency T3 (for example, T3=5%) then the cell frequency value is replaced with a "T", otherwise it is replaced with an "F".

Table 5 shown an example T/F table. For instance, in Row 9, let's assume that feature testosterone_production has been found to have a frequency of more than 5%, hence a "T" is inserted. Similarly for tcf4 in row 14.

The result 676, 860 of the Feature Selection step 666 is either an un-ordered list (e.g. [feature1, feature5, feature12 . . . feature_n]) or an ordered list according to some scoring criterion which is specific to the selected Feature Selection method when supervised Feature Selection is used (if an unsupervised Feature Selection method is used, it reduces only the feature space, e.g. from 500 features to only 120 without significant loss of information). The Supervised Feature Selection Algorithm takes into consideration a response variable (i.e. a Symptom or a group of Symptoms) and identifies the most relevant Features to the response variable (i.e. a Symptom, Syndrome or group of Symptoms).

In the present exemplary embodiment, the analysis is a Classification Analysis problem (looking at which features are relevant to a disease or symptom(s) in a syndrome. The feature selection method outputs the following in an exemplary scenario:

feature1=0.89
feature12=0.80
feature23=0.74
feature4=0.5
. . . .

The number next to each feature suggests the proportion of cases that each feature was found to be relevant to the target column (in our example the targets are the symptoms). Therefore feature1 appears to be highly relevant, followed by feature12, followed by feature23, etc. and are output 676 in an ordered list.

The HOTSPOT algorithm learns a set of rules that maximize/minimize a Response variable/value of interest. These rules may be displayed in a tree-like structure. With a nominal response feature, it looks for segments of the data where there is a high probability of a minority value occurring, given the constraint of a minimum support. For a numeric response feature, it may find segments where this occurrence is higher on average than in the whole data set. This algorithm is similar in spirit to the PRIM bump hunting algorithm described by Friedman and Fisher (1999).

In an exemplary embodiment, before the HOTSPOT algorithm is applied to the data, the calculated frequency table (Table 1) 655 is converted into a new table (T/F Table) where frequencies are replaced by "T" for "True" and "F" for "False". If any cell on the frequency table is larger than a given threshold frequency T3 (for example, T3=2%) then the cell frequency value is replaced with a "T", otherwise it is replaced with an "F".

Table 5 shown an example T/F table. For instance, in Row 9, let's assume that testosterone_production has been found to have a frequency of more than 2%, hence a "T" is inserted. Similarly for feature tcf4 in row 14.

TABLE 5

Example T/F table.

| Row ID | taurine | tbars | tcf4 | testosterone_production | tetrahydrobiopte . . . | tgr5 | th1th2 |
|---|---|---|---|---|---|---|---|
| Row 9 | F | F | F | T | F | F | F |
| Row 10 | F | F | F | F | F | F | F |
| Row 11 | F | F | F | F | F | F | F |
| Row 12 | F | F | F | F | F | F | F |
| Row 13 | F | F | F | F | F | F | F |
| Row 14 | F | F | T | F | F | T | F |
| Row 15 | F | F | F | F | F | T | F |
| Row 16 | F | F | F | F | F | F | F |
| Row 17 | T | T | F | F | T | F | F |
| Row 18 | T | F | F | F | F | T | F |
| Row 19 | F | F | F | F | F | F | F |
| Row 20 | F | F | F | F | F | F | F |
| Row 21 | F | F | T | F | F | F | F |
| Row 22 | F | F | F | F | F | F | F |
| Row 23 | F | F | F | F | F | F | F |
| Row 24 | F | F | F | F | F | F | F |
| Row 25 | F | F | F | F | F | F | F |
| Row 26 | F | T | F | F | F | F | F |
| Row 27 | F | F | F | T | F | T | F |
| Row 28 | F | F | F | F | F | F | F |
| Row 29 | F | F | F | F | F | F | F |
| Row 30 | F | F | F | F | F | F | F |
| Row 31 | F | F | T | T | F | F | T |

The HOTSPOT algorithm may be used to classify medical topics and may, therefore, be used for any response feature, such as a disease, symptom, syndrome, or other medical topic.

An Association Rule Analysis algorithm 669 is also used for discovering relations among large numbers of medical terms associated with a disease or medical syndrome. The algorithm 669 makes use of no response feature and outputs combinations 679 of related medical topics.

In alternative exemplary embodiments of the present invention any number of algorithms may be selected from any of the six categories listed above or from any other category and more than one algorithm can be selected from the same category.

In an alternative exemplary embodiment, Classification Analysis may be used as a DM method. Starting from the topic frequencies of symptoms in Table 6, Symptoms are mapped onto a Feature using a frequency threshold T5 (e.g. 0.5).

TABLE 6 frequencies.csv file containing raw frequencies of topics

| Row ID | 1a1 | ugt1a9 | upr | urea_cycle | uric_acid | urolithiasis | vagus | vcam_1 | vdr |
|---|---|---|---|---|---|---|---|---|---|
| Row 126 | 0 | 0 | 0.58 | 0.15 | 0.034 | 0 | 0 | 0.014 | 0 |
| Row 127 | 0 | 0 | 0.097 | 0.116 | 0.013 | 0.015 | 0 | 0 | 0.017 |
| Row 128 | 0 | 0 | 0 | 0 | 0 | 0 | 0 | 0 | 0 |
| Row 129 | 0 | 0 | 0.252 | 0.166 | 0.057 | 0.015 | 0.025 | 0.213 | 0.28 |
| Row 130 | 0 | 0 | 0.019 | 0.017 | 0.003 | 0 | 0.004 | 0 | 0.017 |
| Row 131 | 0 | 0 | 0.019 | 0.05 | 0.097 | 0.076 | 0.017 | 0.114 | 0.017 |
| Row 132 | 0 | 0 | 0 | 0.033 | 0.003 | 0 | 0.004 | 0.085 | 0.017 |
| Row 133 | 0 | 0 | 0.427 | 0.415 | 0.04 | 0 | 0.071 | 1,335 | 0.805 |
| Row 134 | 0 | 0 | 0 | 0 | 0 | 0 | 0.158 | 0 | 0.857 |
| Row 135 | 0 | 0 | 0.039 | 0.033 | 0.013 | 0.319 | 0.013 | 0.014 | 97,691 |
| Row 136 | 2,637 | 0 | 0 | 0 | 0.007 | 0 | 0 | 0 | 1.7 |
| Row 137 | 0.406 | 0.116 | 0 | 0 | 0 | 0 | 0 | 0.043 | 8,677 |
| Row 138 | 0 | 0.039 | 33 | 0 | 0 | 0 | 0 | 0.057 | 0.875 |
| Row 139 | 0 | 0.136 | 0.066 | 0 | 0.013 | 0 | 0.008 | 0.767 | 0.052 |
| Row 140 | 8,316 | 0 | 5 | 0.024 | 0.015 | 0 | 0 | 0 | 0 |
| Row 141 | 0 | 0 | 0 | 0 | 0 | 0 | 0.038 | 0 | 0.017 |
| Row 142 | 0 | 0.097 | 0.781 | 0.151 | 0 | 0 | 0.013 | 0.17 | 0.035 |
| Row 143 | 0.203 | 0 | 0.399 | 0.024 | 0.152 | 0.267 | 0.043 | 0.017 | |
| Row 144 | 0 | 0 | 0 | 0 | 0 | 0 | 0 | 0 | 0 |
| Row 145 | 0 | 0.33 | 0 | 0.013 | 0.015 | 0.021 | 0.128 | 0.017 | |
| Row 146 | 0 | 0 | 0.017 | 0.044 | 0 | 0.096 | 0.071 | 0.017 | |
| Row 147 | 0.203 | 0.116 | 0.316 | 0.621 | 0.015 | 0.013 | 0.284 | 0.07 | |
| Row 148 | 0.203 | 0.097 | 0.066 | 0.034 | 0 | 0 | 0.057 | 0.21 | |
| Row 149 | 0 | 0.019 | 0.033 | 0.027 | 0 | 0.021 | 0.014 | 0 | |
| Row 150 | 0 | 0.058 | 0.814 | 1,387 | 0.061 | 0.054 | 0.085 | 0.07 | |
| Row 151 | 0 | 0 | 0.05 | 0.306 | 0.137 | 0.008 | 0 | 0 | |
| Row 152 | 0 | 0 | 0.182 | 1,182 | 0.046 | 0.042 | 0.071 | 0.017 | |
| Row 153 | 0 | 0.019 | 0 | 0.003 | 0 | 0 | 0 | 0 | |
| Row 154 | 0 | 0.019 | 0.083 | 0.01 | 0 | 0.013 | 0 | 0 | |
| Row 155 | 0 | 0.64 | 0 | 0 | 0 | 0 | 0.014 | 0 | |
| Row 156 | 0 | 0.291 | 0.15 | 0.232 | 0.015 | 0.033 | 1,107 | 0.07 | |
| Row 157 | 0 | 0.78 | 0 | 0.013 | 0 | 0.021 | 0.625 | 0.245 | |
| Row 158 | 0 | 0.252 | 0.083 | 0.094 | 0 | 0.013 | 0.256 | 0.017 | |
| Row 159 | 0 | 0.058 | 0.066 | 0.222 | 0.122 | 0.008 | 0.256 | 0.017 | |

| Row ID | vitami . . . | vitami . . . | vitami . . . | xanthi | xbp1 | zinc_d . . . | zinc_s | Symp. |
|---|---|---|---|---|---|---|---|---|
| Row 126 | 0.935 | 0 | 0.027 | 0.053 | 0.138 | 0.028 | 0.128 | F |
| Row 127 | 0.644 | 0.023 | 0.065 | 0.009 | 0.069 | 0.255 | 0.064 | F |
| Row 128 | 0 | 0.004 | 0 | 0 | 0 | 0.028 | 0 | F |
| Row 129 | 0.021 | 0.236 | 0.022 | 0.018 | 0.345 | 0.304 | 0.256 | F |
| Row 130 | 0 | 0.031 | 0.016 | 0.018 | 0 | 0.111 | 0.064 | F |
| Row 131 | 0.021 | 0.043 | 0.043 | 0.044 | 0 | 0.083 | 0.021 | F |
| Row 132 | 0 | 23 | 0.016 | 0.026 | 0.069 | 0.055 | 0.043 | F |
| Row 133 | 0 | 1.17 | 119 | 0.852 | 0.207 | 0.249 | 0.043 | T |
| Row 134 | 0 | 0.275 | 0.005 | 0 | 0 | 0 | 0 | F |
| Row 135 | 0 | 8,143 | 0.038 | 0 | 0.069 | 0.028 | 0.021 | F |
| Row 136 | 0 | 0.074 | 0.07 | 0.009 | 0 | 0.028 | 0 | F |
| Row 137 | 0 | 1,252 | 0.038 | 0.018 | 0.138 | 0.083 | 0.043 | F |
| Row 138 | 0 | 0.043 | 0 | 0.009 | 0.069 | 0 | 0 | F |
| Row 139 | 0.042 | 0.097 | 0.022 | 0.026 | 0 | 0.304 | 0.277 | T |
| Row 140 | 0.021 | 0.008 | 0.005 | 0.035 | 0 | 0 | 0 | F |
| Row 141 | 0.021 | 0 | 0.005 | 0.009 | 0 | 0 | 0.021 | T |
| Row 142 | 0.125 | 0.205 | 0.087 | 0.264 | 0.207 | 0.055 | 0.149 | T |
| Row 143 | 0.125 | 0.132 | 0.119 | 0.026 | 0 | 2,379 | 0.83 | T |
| Row 144 | 0 | 0 | 0 | 0 | 0 | 0.028 | 0 | F |
| Row 145 | 0 | 0.019 | 0.005 | 0.062 | 0.552 | 0.028 | 0 | F |
| Row 146 | 0.042 | 0.004 | 0.032 | 0.149 | 0 | 0.055 | 0.021 | T |
| Row 147 | 0.145 | 0.047 | 0.585 | 1,775 | 0.138 | 0.36 | 0.809 | T |
| Row 148 | 0 | 0.05 | 0.054 | 0.211 | 0.138 | 0.055 | 0.106 | F |
| Row 149 | 0.104 | 0.023 | 0.005 | 0.009 | 0.069 | 0 | 0.021 | T |
| Row 150 | 0.291 | 0.217 | 0.076 | 0.677 | 0 | 0 | 0.192 | T |
| Row 151 | 0 | 0.054 | 0 | 0 | 0 | 0.055 | 0 | F |
| Row 152 | 0.021 | 0.012 | 0.022 | 1,318 | 0 | 0.055 | 0.021 | F |
| Row 153 | 0 | 0 | 0 | 0 | 0.069 | 0 | 0 | F |
| Row 154 | 0 | 0.008 | 0.011 | 0 | 0 | 0 | 0 | F |
| Row 155 | 0 | 0.08 | 0.054 | 0 | 0.345 | 0 | 0 | F |
| Row 156 | 0.125 | 0.182 | 0.157 | 0.272 | 0.967 | 0.221 | 0.405 | T |
| Row 157 | 0.042 | 0.132 | 0.016 | 0.018 | 0.207 | 0.194 | 0.128 | T |

TABLE 6-continued frequencies.csv file containing raw frequencies of topics

| Row 158 | 0.042 | 0.062 | 0.038 | 0.097 | 1,657 | 0.249 | 0.128 | T |
| Row 159 | 0.021 | 0.101 | 0.038 | 0.044 | 0.276 | 0.332 | 0.319 | T |

As an example we have the features named insomnia.csv and orthostatic_intolerance.csv that contain PUBMED entries for the relevant symptoms. The frequencies.csv of Table 6 is created by matching all CSV files against each other and will therefore contain the matched frequencies of insomnia and orthostatic intolerance. Selecting a frequency threshold of e.g. 0.5 and checking across each row to find any symptoms with a frequency higher than the 0.5 threshold, the corresponding cell at the last column is set to "T" if at least one frequency in the selected row is above the 0.5 threshold. Otherwise, it is set to "F".

In the example of Table 6, row 133 is set to "T". Additionally, pre-processing may be added in variations of the present exemplary embodiment, like:
  a) filtering attributes having low variance (i.e. attributes that do not change too much)
  b) filtering attributes that are highly correlated with each other.
  c) transposing the input to less features (perform PCA Analysis)
  d) discretizing features The resulting symptoms need to be balanced so as to come up with unbiased results. For example, in order for the algorithm to be able to learn efficiently the problem at hand, if the algorithm has 1000 cases of Symptom=TRUE but only 15 cases of Symptom=FALSE then it will be very hard to identify which features differentiate Symptom vs. no-Symptom. For this reason additional asymptomatic data should be used or should be created by any technique known in prior art. By means of example, resampling and class weighting/cost effective learning may be used.

For resampling, let's assume a distribution of 1000 Total Instances, of which 700 (i.e. 70%) are Non-Symptom occurrences and 300 (i.e. 30%) are Symptom occurrences. The method may either:
  a) subsample the majority class (i.e. the "Non-Symptom) to produce 300 (i.e. 50%) Non-Symptom occurrences and 300 (50%) Symptom occurrences by removing 400 records from the Non-Symptom class. The choice of algorithm may be among random majority under-sampling with replacement, extraction of majority-minority Tomek links, under-sampling with Cluster Centroids, NearMiss-(1 & 2 & 3), Condensed Nearest Neighbor, One-Sided Selection, Neighborhood Cleaning Rule, Edited Nearest Neighbors, Instance Hardness Threshold, Repeated Edited Nearest Neighbors, AllKNN, or any other similar technique known in prior art
  b) oversample using the Random minority over-sampling with replacement, Synthetic Minority Oversampling TEchnique (SMOTE), bSMOTE(1 & 2)—Borderline SMOTE of types 1 and 2, SVM SMOTE—Support Vectors SMOTE, ADAptive SYNthetic (ADASYN) sampling approach for imbalanced learning, or any other similar technique known in prior art
  c) Over-sampling followed by under-sampling using the SMOTE+Tomek links, SMOTE+ENN or other techniques known in prior art
  d) Ensemble sampling using EasyEnsemble, BalanceCascade or any other similar technique known in prior art.

For Class Weighting/Cost-sensitive Learning, a cost-sensitive classifier is used where a cost is assigned to each misclassification. A higher cost is assigned to cases where the algorithm misclassifies a Symptom for a Non-Symptom; this is the most frequent error in the present example there are more non-symptom cases on the training data than there are symptom cases. Class-weighting enables the adjustment of the importance of each class, e.g. the "SYMPTOM" class can be adjusted to have a greater importance. Various other modifications and techniques may be used.

In another exemplary embodiment, Data Partitioning (e.g. the Holdout method or the K-Fold Cross-Validation method or any other Data Partitioning method in a variation of the current exemplary embodiment) is used as a ML method where it is applied on a portion of Data (say 75%, known as the Training Set) for Learning and the rest 25% is used to evaluate the algorithm's performance (the 25% is known as the Validation Set). First, the learning set is fed to the method to train it and then the validation set is used to calculate how many times the method correctly predicts the Symptom (True or False) attribute. By means of example, the F1 score is used in this evaluation.

In alternative embodiments, any of the following classification metrics may be used:
  accuracy
  average_precision
  f1
  f1_micro
  f1_macro
  f1_weighted
  f1_samples
  neg_log_loss
  precision'
  recall
  roc_auc The above methods are used for assessing the predictive performance of ML Algorithms. In an alternative exemplary embodiment, the method looks at the features that were selected by the ML Algorithms which have a high predictive value (e.g. f1 measure >0.8) instead of considering features from average-performing ML Algorithms.

ML algorithms have a number of parameters, for example Support Vector Machines (SVM) use the C parameter as the penalty parameter and the "degree" parameter which denotes the degree of the polynomial function.

In the present invention a number of iterations may be run for each ML Algorithm using different parameter settings and check the observed performance of the algorithms after each iteration. This parameter optimization may be implemented in alternative exemplary embodiments (e.g. Randomized Parameter Optimization, Exhaustive Grid Search, Nested-Cross validation, etc.) to optimize each ML algorithm parameter settings.

Since the different algorithms used from the first four classes 662, 664, 666, 668 produce results in different representations, these results need to be converted into a compatible format that allows their combination 690 into the final result 695 of the present invention.

For example, the algorithms 662, 664, 666, 668 may produce one of the following types of partial results 672, 674, 676, 678:
  a) Ordered list of medical topics with associated confidence values having a significant confidence distance from each other (offering significant information).
  b) Ordered list of medical topics with associated confidence values having a uniform confidence distance from each other (i.e. offering limited information).
  c) Ordered list of medical topics with associated confidence values, where the ordering of the topics and the number of topics are different among algorithms
  d) Ordered list of grouped medical topics without any other confidence values associated with the topics (offering frequency of occurrence information
  e) Unordered list of any of the above Table 7 shows example partial and combined result output from various DM, NA, HOTSPOT, and Feature Selection algorithms. These results may originate from Group 1 Analysis or Group2 Analysis as previously presented. Example 1b or Example 2 corresponds among other results to the results of Group3 and Group4.

TABLE 7

Example partial results 672, 674, 676, 678 outputted from various algorithms.

| TOPIC | Importance | min-max norm | inv_levels |
|---|---|---|---|
| EXAMPLE1a | | | |
| topic1 | 0.8 | 1 | |
| topic2 | 0.4 | 0.428571429 | |
| topic3 | 0.2 | 0.142857143 | |
| topic4 | 0.1 | 0 | |
| EXAMPLE1b | | | |
| topic2 | 1 | 1 | |
| topic3 | 0.9 | 0.875 | |
| topic1 | 0.4 | 0.25 | |
| topic4 | 0.2 | 0 | |
| EXAMPLE2 | | | |
| topic2 | 4 | 1 | |
| topic3 | 3 | 0.66666667 | |
| topic1 | 2 | 0.33333333 | |
| topic4 | 1 | 0 | |
| EXAMPLE3 | | | |
| topic2 | 1 | 1 | 3 |
| topic3 | 1 | 1 | 3 |
| topic4 | 2 | 0.5 | 2 |
| topic1 | 3 | 0 | 1 |
| EXAMPLE4 | | | |
| topic2 | 342 | 1 | |
| topic3 | 112 | 0.303030303 | |
| topic1 | 58 | 0.139393939 | |
| topic4 | 12 | 0 | |

| Combined Results TOPIC | Normalized Importance |
|---|---|
| topic1 | 1.66 |
| topic2 | 4.4 |
| topic3 | 2.83 |
| topic4 | 0.9 |

Example 1a shows the output of an algorithm (e.g. Randomized Logistic Regression, XGBoost, Random Forests, . . . ) ranking topics in the range [1 . . . 0] of importance score, 1 being the highest ranking. As with any ML Algorithm, it has an associated Accuracy Score (such as F1). The method may then consider features from Algorithms that had a high rate of Prediction Accuracy such as F1>85% In order to be able to compare and combine these results with the results of other algorithms, MM-Max normalization (shown in Equation 1) is used to normalize them while preserving their ranking; in alternative exemplary embodiments, different normalization algorithms may be used instead.

$$z = (x - \min(x))/(\max(x) - \min(x)) \quad \text{(Equation 1)}$$

Example 1b, shows the output of another algorithm (from the same category of algorithms as in Example 1a) which produces an output containing the same four topics as Example 1a but differently ranked and with a different importance score which is then normalized.

Example 2 shows the output of an algorithm (e.g. Randomized Logistic Regression, XGBoost, Random Forests, etc.) which contains the same four topics as in Examples 1 but in a different order. The output simply contains the ordering (1 . . . 4), i.e. first, second, etc. of the four topics and no confidence values. However, as in the other examples we are using the ranking from highest score to lowest score the (1 . . . 4) ranking needs to be normalized using Equation 2.

$$\text{High-to-Low-Ranking} = (\#\_of\_Topics + 1) - \text{Order\_of\_Appearance} \quad \text{(Equation 2)}$$

The output of Equation 2 for Topic 2 is (4+1)−1=4. Similarly for the other topics. These values are then normalized.

Example 3 shows the output of an algorithm (e.g. Bayes Network) that creates levels of importance. In this case three levels are found (1, 2, 3) and topic2 and topic3 are on the first level, topic4 on the second level and topic1 on the third level. In analogy to Example 2, the levels need to be normalized (i.e. inversed here; shown in column "inv_levels") so as to associate the highest level topic with the highest level (i.e. highest number) and be in line with the representation followed in other examples. These are then Min-Max normalized in the interval [1 . . . 0].

Example 4 shows the output of different algorithms running the same classification problem and counts the occurrences of each feature in the solution. For instance:
  Algorithm 1 outputs [feat1,feat2,feat5,feat7]
  Algorithm 2 outputs [feat2,feat5,feat12] and
  Algorithm 3 outputs [feat2, feat12,feat25]

Counting the frequencies of occurrence of the various features outputted from the 3 algorithms, we get the following results:
  feat2=3 occurrences
  feat12=2 occurrences
  feat5=2 occurrences
  . . . and so on . . . .

These frequencies of occurrence are then Min-Max normalized and ready to be combined with the other example results.

In an alternative exemplary embodiment, Example 4 contains the results obtained from running the same algorithm several times over the same dataset but using different parameters or different training/testing samples.

The above different types of outputs necessitate the post-processing 682, 684, 686, 688 of the partial results 672, 674, 676, 678 to convert them into a uniform representation before they can be combined 690 into a final result 695. This is done using any feature Scaling method (such as Min-Max scaling in the previous examples) or any other Transformation method.

In this exemplary embodiment the Min-Max scaling was used alone or together with re-ordering of the partial results.

The post-processes partial results 682, 684, 686, 688 can now be combined 690 into the final result 695 simply by adding the normalized confidence values and outputting the new (combined) confidence value together with the associated medical term in an ordered list. Referring again to Table 7, the combined results show the normalized importance score for each of the four topics, revealing that Topic 2 is the most important topic as it has the highest score. The ranking produced from the combined results is different from (at least some of) the individual (partial) result rankings.

In a variation of this exemplary embodiment, the normalized partial results are weighted so as to reflect their confidence or importance and contribute accordingly to the computation of the final result 695. The weighting may be done using any known algorithm and assign any type of weight of any magnitude. These weights give higher importance e.g. to partial results of topics with associated confidence values having a significant confidence distance from each other (e.g. Examples 1a, 1b, 4) as opposed to results of nearly uniform confidence distance from each other (Example 2), unordered lists of topics, or results of grouped medical topics (Example 3) without any other confidence values associated with the topics.

Results 679, 680 are output 698 as lists of biological elements and/or groups of symptoms alongside combined results 690. The resulting outcome of the proposed innovative solution is an analysis of biological elements from a different analysis viewpoint and consequently the outcome identifies more correlations between biological elements, environmental and nutritional factors associated with diseases and medical syndromes, and patterns of interaction between groups of biological elements, environmental and nutritional factors, diseases and medical syndromes than those identified in prior art. An important contribution of the proposed innovative solution is the identification of patterns of interaction and associations between groups of biological elements and symptoms, and diseases and medical syndromes, in addition to the simple identification of biological elements associated with diseases and medical syndromes as in prior art. For this reason, additional associations and interactions are identified exceeding by far what is achieved in prior art.

The above exemplary embodiments are intended for use either as a standalone method, or as part of other scientific and business methods, processes and systems.

The above exemplary embodiment descriptions are simplified and do not include an exhaustive listing of hardware and software elements that are used in the embodiments but which are not part of the current invention, are not needed for the understanding of the embodiments, and are obvious to any user of ordinary skill in related art. Furthermore, variations of the described method, system architecture, and software architecture are possible, where, for instance, method steps, and hardware and software elements may be rearranged, omitted, or new added.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

In one or more exemplary embodiments, the functions described may be implemented in hardware, software, firmware, or any combination thereof. If implemented in software, the functions may be stored on or transmitted over as one or more instructions or code on a computer readable medium and may be run on a single computing device or system, or be divided among more than one computing devices or systems, or on cloud infrastructures. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer or any other device or apparatus operating as a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The invention claimed is:

1. A computer implemented method of discovering biological topics, symptoms and environmental and nutritional factors related to diseases, medical syndromes and biological functions, wherein the biological topics comprise genes, biological molecules, and biological pathways, the computer implemented method comprising:

querying a database for at least one of a biological topic, a symptom, an environmental factor, a nutritional factor, a disease, a medical syndrome, and a biological function to produce at least one query result;

preprocessing the at least one query result for the at least one of the biological topic, the symptom, the environmental factor, the nutritional factor, the disease, the medical syndrome, and the biological function to produce at least one preprocessed query result, wherein the preprocessing comprises at least one of natural language processing, normalization, and natural language understanding;

transforming the at least one preprocessed query result in a different feature space to produce at least one transformed result;

applying a plurality of data mining algorithms to the at least one transformed result to produce a plurality of outcomes of the data mining algorithms, wherein:

(i) each of the data mining algorithms produces outcomes of one of the following types: (a) an ordered list of biological topics, symptoms, environmental or nutritional factors associated with diseases, medical syndromes or biological functions with association confidence values having a significant confidence distance from each other, (b) an ordered list of biological topics, symptoms, environmental or nutritional factors associated with diseases, medical syndromes or biological functions with association confidence values having a uniform confidence distance from each other, (c) an ordered list of biological topics, symptoms, environmental or nutritional factors associated with diseases, medical syndromes or biological functions with association confidence values, wherein the ordering of the topics and the number of topics are different among algorithms, (d) and ordered list of grouped biological topics, symptoms, environmental or nutritional factors associated with diseases, medical syndromes or biological functions without any association confidence values, the ordered list comprising frequency of occurrence information, and (e) an unordered list of grouped biological topics, symptoms, environmental or nutritional factors associated with diseases, medical syndromes or biological functions;

post-processing the plurality of outcomes of the data mining algorithms; and selectively combining the plurality of outcomes of the data mining algorithms into a single result, wherein the selectively combining produces (a) biological topics, symptoms, environmental factors, nutritional factors associated with diseases, medical syndromes and biological functions, and (b) patterns of interaction and effects of interaction between groups of biological topics, symptoms, environmental factors, nutritional factors associated with diseases, medical syndromes and biological functions.

2. The computer implemented method of claim 1, further comprising:

applying at least one algorithm to produce hypotheses on associations between (a) medical topics, symptoms, environmental and nutritional factors and (b) groups of medical topics, symptoms, environmental and nutritional factors with diseases, medical syndromes and biological functions.

3. The computer implemented method of claim 1, wherein the preprocessing produces nodes used by a network analysis algorithm.

4. The computer implemented method of claim 1, wherein the step of selectively combining the plurality of outcomes of the data mining algorithms comprises normalization of the plurality of outcomes of the data mining algorithms for producing a ranking of the combined results, and wherein the ranking of the combined result is different from a ranking of the plurality of outcomes of the data mining algorithms and the ranking of the combined result is based on the confidence values produced by each algorithm.

5. The computer implemented method of claim 4, wherein the combined result is used to identify active drug substances having an effect on diseases, medical syndromes and biological functions.

6. The computer implemented method of claim 4, wherein the combined result is used to identify symptoms, groups of symptoms, and biological pathways associated with symptoms or groups of symptoms.

7. The computer implemented method of claim 4, wherein the combined result is used to verify experimental results and theories.

8. The computer implemented method of claim 1, wherein a network analysis algorithm is used to identify important biological topics, symptoms and environmental and nutritional factors related to diseases, medical syndromes and biological functions by selecting those biological topics, symptoms and environmental and nutritional factors that have the highest score in at least one network analysis metric, wherein the at least one network analysis metric comprises centrality, degree, betweenness, and closeness.

9. The computer implemented method of claim 8, wherein a result of the identification is used to guide biological research by indicating biological topics for research.

10. A computing device configured to discover biological topics, symptoms and environmental and nutritional factors related to diseases, medical syndromes and biological functions, wherein the biological topics comprise genes, biological molecules, and biological pathways, the computing device comprising:

a memory; and a processor operatively coupled to the memory, the processor configured to perform the steps of:

querying a database for at least one of a biological topic, a symptom, an environmental factor, a nutritional factor, a disease, a medical syndrome, and a biological function to produce at least one query result;

preprocessing the at least one query result for the at least one of the biological topic, the symptom, the environmental factor, the nutritional factor, the disease, the medical syndrome, and the biological function to produce at least one preprocessed query result, wherein the preprocessing comprises at least one of natural language processing, normalization, and natural language understanding;

transforming the at least one preprocessed query result in a different feature space to produce at least one transformed result;

applying a plurality of data mining algorithms to the at least one transformed result to produce a plurality of outcomes of the data mining algorithms, wherein:

(i) each of the data mining algorithms produces outcomes of one of the following types: (a) an ordered list of biological topics, symptoms, environmental or nutritional factors associated with diseases, medical syndromes or biological functions with association confidence values having a significant confidence distance from each other, (b) an ordered list of biological topics, symptoms, environmental or nutritional factors associated with diseases, medical syndromes or biological functions with association confidence values having a uniform confidence distance from each other, (c) an ordered list of biological topics, symptoms, environmental or nutritional factors associated with diseases, medical syndromes or biological functions with association confidence values, wherein the ordering of the topics and the number of topics are different among algorithms, (d) and ordered list of grouped biological topics, symptoms, environmental or nutritional factors associated with diseases, medical syndromes or biological functions without any association confidence values, the ordered list comprising frequency of occurrence information, and (e) an unordered list of grouped biological topics, symptoms, environmental or nutritional factors associated with diseases, medical syndromes or biological functions;

post-processing the plurality of outcomes of the data mining algorithms; and selectively combining the plurality of outcomes of the data mining algorithms into a single result, wherein the selectively combining produces (a) biological topics, symptoms, environmental factors, nutritional factors associated with diseases, medical syndromes and biological functions, and (b) patterns of interaction and effects of interaction between groups of biological topics, symptoms, environmental factors, nutritional factors associated with diseases, medical syndromes and biological functions.

11. The computing device of claim 10, wherein the processor is further configured to apply at least one algorithm to produce hypotheses on associations between (a) medical topics, symptoms, environmental and nutritional factors and (b) groups of medical topics, symptoms, environmental and nutritional factors with diseases, medical syndromes and biological functions.

12. The computing device of claim 10, wherein the preprocessing produces nodes used by a network analysis algorithm.

13. The computing device of claim 10, wherein the step of selectively combining the plurality of outcomes of the data mining algorithms comprises normalization of the plurality of outcomes of the data mining algorithms for producing a ranking of the combined result, and wherein the ranking of the combined result is different from a ranking of the plurality of outcomes of the data mining algorithms and the ranking of the combined result is based on the confidence values produced by each algorithm.

14. The computing device of claim 10, wherein the processor is further adapted to use a network analysis algorithm to identify important biological topics, symptoms and environmental and nutritional factors related to diseases, medical syndromes and biological functions by selecting those biological topics, symptoms and environmental and nutritional factors that have the highest score in at least one network analysis metric, wherein the at least one network analysis metric comprises centrality, degree, betweenness, and closeness.

15. The computing device of claim 14, wherein a result of the identification is used to guide biological research by indicating biological topics for research.

16. The computing device of claim 14, wherein the combined result is used for at least one of:

identifying active drug substances having an effect on diseases, medical syndromes and biological functions;

identifying symptoms, groups of symptoms, and biological pathways associated with symptoms or groups of symptoms; and verifying experimental results and theories.

17. A non-transitory computer program product that causes a computing device to discover biological topics, symptoms and environmental and nutritional factors related to diseases, medical syndromes and biological functions, wherein the biological topics comprise genes, biological molecules, and biological pathways, the non-transitory computer program product having instructions to:

query a database for at least one of a biological topic, a symptom, an environmental factor, a nutritional factor, a disease, a medical syndrome, and a biological function to produce at least one query result;

preprocess the at least one query result for the at least one of the biological topic, the symptom, the environmental factor, the nutritional factor, the disease, the medical syndrome, and the biological function to produce at least one preprocessed query result, wherein the preprocessing comprises at least one of natural language processing, normalization, and natural language understanding;

transform the at least one preprocessed query result in a different feature space to produce at least one transformed result;

apply a plurality of data mining algorithms to the at least one transformed result to produce a plurality of outcomes of the data mining algorithms, wherein:

(i) each of the data mining algorithms produces outcomes of one of the following types: (a) an ordered list of biological topics, symptoms, environmental or nutritional factors associated with diseases, medical syndromes or biological functions with association confidence values having a significant confidence distance from each other, (b) an ordered list of biological topics, symptoms, environmental or nutritional factors associated with diseases, medical syndromes or biological functions with association confidence values having a uniform confidence distance from each other, (c) an ordered list of biological topics, symptoms, environmental or nutritional factors associated with diseases, medical syndromes or biological functions with association confidence values, wherein the ordering of the topics and the number of topics are different among algorithms, (d) and ordered list of grouped biological topics, symptoms, environmental or nutritional factors associated with diseases, medical syndromes or biological functions without any association confidence values, the ordered list comprising frequency of occurrence information, and (e) an unordered list of grouped biological topics, symptoms, environmental or nutritional factors associated with diseases, medical syndromes or biological functions;

post-process the plurality of outcomes of the data mining algorithms; and selectively combine the plurality of outcomes of the data mining algorithms into a single result, wherein the selectively combining produces (a) biological topics, symptoms, environmental factors, nutritional factors associated with diseases, medical syndromes and biological functions, and (b) patterns of interaction and effects of interaction between groups of biological topics, symptoms, environmental factors, nutritional factors associated with diseases, medical syndromes and biological functions.

18. The non-transitory computer program product of claim 17, wherein the non-transitory computer program product has further instructions to apply at least one algorithm to produce hypotheses on associations between (a) medical topics, symptoms, environmental and nutritional factors and (b) groups of medical topics, symptoms, environmental and nutritional factors with diseases, medical syndromes and biological functions.

19. The non-transitory computer program product of claim 17, wherein the preprocessing produces nodes used by a network analysis algorithm.

20. The non-transitory computer program product of claim 17, wherein the step of selectively combining the plurality of outcomes of the data mining algorithms comprises normalization of the plurality of outcomes of the data mining algorithms for producing a ranking of the combined result, and wherein the ranking of the combined result is different from a ranking of the plurality of outcomes of the data mining algorithms and the ranking of the combined result is based on the confidence values produced by each algorithm.

* * * * *

UNITED STATES PATENT AND TRADEMARK OFFICE
CERTIFICATE OF CORRECTION

PATENT NO. : 10,748,663 B2  
APPLICATION NO. : 15/966454  
DATED : August 18, 2020  
INVENTOR(S) : Efthymios Kalafatis Page 1 of 1

It is certified that error appears in the above-identified patent and that said Letters Patent is hereby corrected as shown below:

In the Drawings

Sheet 7, FIG. 8, the cluster element labeled "glucose_6_ phospahatase" should be changed to --glucose_6_phosphatase--.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*